(12) United States Patent
Miller et al.

(10) Patent No.: US 8,518,457 B2
(45) Date of Patent: Aug. 27, 2013

(54) USE OF INHALED GASEOUS NITRIC OXIDE AS A MUCOLYTIC AGENT OR EXPECTORANT

(75) Inventors: Christopher C. Miller, North Vancouver (CA); Douglas R. Hole, Edmonton (CA); Bruce R Murray, Tofield (CA); Bryan Perry, West Seneca, NY (US)

(73) Assignee: Pulmonox Technologies Corporation (CA)

( * ) Notice: Subject to any disclaimer, the term of this patent is extended or adjusted under 35 U.S.C. 154(b) by 17 days.

(21) Appl. No.: 11/595,108

(22) Filed: Nov. 10, 2006

(65) Prior Publication Data

US 2007/0104653 A1    May 10, 2007

Related U.S. Application Data

(63) Continuation-in-part of application No. PCT/US2005/016428, filed on May 11, 2005.

(60) Provisional application No. 60/569,888, filed on May 11, 2004.

(51) Int. Cl.
*A61K 33/00* (2006.01)
*A61M 16/00* (2006.01)
*A61M 16/10* (2006.01)

(52) U.S. Cl.
USPC .................. 424/718; 128/200.24; 128/207.18

(58) Field of Classification Search
None
See application file for complete search history.

(56) References Cited

U.S. PATENT DOCUMENTS

| | | |
|---|---|---|
| 3,036,584 A | 5/1962 | Lee |
| 3,192,106 A | 6/1965 | Bracken et al. |
| 4,127,121 A | 11/1978 | Westenskow et al. |
| 4,191,952 A | 3/1980 | Schreiber et al. |
| 4,224,941 A | 9/1980 | Stivala |
| 4,328,823 A | 5/1982 | Schreiber |
| 4,336,798 A | 6/1982 | Beran |
| 4,345,612 A | 8/1982 | Koni et al. |
| 4,442,856 A | 4/1984 | Betz et al. |
| 4,608,041 A | 8/1986 | Nielsen |

(Continued)

FOREIGN PATENT DOCUMENTS

| | | |
|---|---|---|
| DE | 003713396 A1 | 11/1998 |
| EP | 0640356 A1 | 3/1995 |

(Continued)

OTHER PUBLICATIONS

Shale et al. (Eur. Resp. J 2004, 23, 797-798).*

(Continued)

*Primary Examiner* — Ernst Arnold

(57) ABSTRACT

Methods and devices for treating excess mucus accumulation in mammals by administering gaseous inhaled nitric oxide or nitric oxide releasing compounds as a mucolytic agent or expectorant are provided. Delivery of gaseous nitric oxide can be made nasally or orally and is preferably substantially coincident with inhalation of the mammal or based on a synchronous parameter of the mammal's respiratory cycle. Varying therapeutic profiles may be used for the delivery of gaseous nitric oxide depending on the severity of the excess mucus accumulation. Parameters for the therapeutic profiles may include flow rate of nitric oxide containing gas, duration of administration of nitric oxide containing gas, number of breaths for which nitric oxide containing gas is to be administered, and concentrations of therapeutic NO delivered to the airways.

25 Claims, 5 Drawing Sheets

(56) References Cited

U.S. PATENT DOCUMENTS

| | | |
|---|---|---|
| 4,611,590 A | 9/1986 | Ryschka et al. |
| 4,770,168 A | 9/1988 | Rusz et al. |
| 4,905,685 A | 3/1990 | Olsson et al. |
| 4,954,526 A | 9/1990 | Keefer |
| 5,154,697 A | 10/1992 | Loori |
| 5,155,137 A | 10/1992 | Keefer et al. |
| 5,159,924 A | 11/1992 | Cegielski et al. |
| 5,197,462 A | 3/1993 | Falb et al. |
| 5,396,882 A | 3/1995 | Zapol |
| 5,423,313 A | 6/1995 | Olsson et al. |
| 5,427,797 A | 6/1995 | Frostell et al. |
| 5,485,827 A | 1/1996 | Zapol et al. |
| 5,514,204 A | 5/1996 | Sheu et al. |
| 5,519,020 A | 5/1996 | Smith et al. |
| 5,531,218 A | 7/1996 | Krebs |
| 5,536,241 A | 7/1996 | Zapol |
| 5,558,083 A | 9/1996 | Bathe et al. |
| 5,570,683 A | 11/1996 | Zapol |
| 5,574,068 A * | 11/1996 | Stamler et al. ............. 514/562 |
| 5,615,669 A | 4/1997 | Olsson et al. |
| 5,632,981 A | 5/1997 | Saavedra et al. |
| 5,648,101 A | 7/1997 | Tawashi |
| 5,650,442 A | 7/1997 | Mitchell et al. |
| 5,651,358 A | 7/1997 | Briend et al. |
| 5,656,589 A * | 8/1997 | Stossel et al. ............. 424/94.6 |
| 5,676,963 A | 10/1997 | Keefer et al. |
| 5,688,236 A | 11/1997 | Gragg |
| 5,692,497 A | 12/1997 | Schnitzer et al. |
| 5,700,830 A | 12/1997 | Korthuis et al. |
| 5,713,349 A | 2/1998 | Kearney |
| 5,722,392 A | 3/1998 | Skimming et al. |
| 5,732,693 A | 3/1998 | Bathe et al. |
| 5,765,548 A | 6/1998 | Perry |
| 5,789,447 A | 8/1998 | Wink, Jr. et al. |
| 5,810,795 A | 9/1998 | Westwood |
| 5,814,666 A | 9/1998 | Green et al. |
| 5,814,667 A | 9/1998 | Mitchell et al. |
| 5,823,180 A | 10/1998 | Zapol |
| 5,830,436 A * | 11/1998 | Ghio et al. ............. 424/45 |
| 5,834,030 A | 11/1998 | Bolton |
| 5,837,736 A | 11/1998 | Mitchell et al. |
| 5,839,433 A | 11/1998 | Higgenbottam |
| 5,840,759 A | 11/1998 | Mitchell et al. |
| 5,845,633 A | 12/1998 | Psaros |
| 5,873,359 A | 2/1999 | Zapol et al. |
| 5,885,621 A | 3/1999 | Head et al. |
| 5,904,938 A | 5/1999 | Zapol et al. |
| 5,918,596 A | 7/1999 | Heinonen |
| 5,957,880 A | 9/1999 | Igo et al. |
| 6,000,403 A | 12/1999 | Cantwell |
| 6,060,020 A | 5/2000 | Piuk et al. |
| 6,063,407 A | 5/2000 | Zapol et al. |
| 6,067,983 A | 5/2000 | Stenzler |
| 6,071,254 A | 6/2000 | Augustine |
| 6,073,627 A | 6/2000 | Sunnen |
| 6,083,209 A | 7/2000 | Marasco, Jr. |
| 6,089,229 A | 7/2000 | Bathe et al. |
| 6,103,275 A | 8/2000 | Seitz et al. |
| 6,109,260 A | 8/2000 | Bathe |
| 6,110,895 A | 8/2000 | Rodgers et al. |
| 6,125,846 A | 10/2000 | Bathe et al. |
| 6,131,572 A | 10/2000 | Heinonen |
| 6,142,147 A | 11/2000 | Head et al. |
| 6,158,434 A | 12/2000 | Lugtigheid et al. |
| 6,160,021 A | 12/2000 | Lerner et al. |
| 6,164,276 A | 12/2000 | Bathe et al. |
| 6,190,704 B1 | 2/2001 | Murrell |
| 6,200,558 B1 | 3/2001 | Saavedra et al. |
| 6,232,336 B1 | 5/2001 | Hrabie et al. |
| 6,270,779 B1 | 8/2001 | Fitzhugh et al. |
| 6,358,536 B1 | 3/2002 | Thomas |
| 6,379,660 B1 | 4/2002 | Saavedra et al. |
| 6,432,077 B1 | 8/2002 | Stenzler |
| 6,472,390 B1 | 10/2002 | Stamler et al. |
| 6,494,314 B1 | 12/2002 | Lamborne et al. |
| 6,511,991 B2 | 1/2003 | Hrabie et al. |
| 6,555,058 B2 | 4/2003 | Kamibayashi et al. |
| 6,571,790 B1 | 6/2003 | Weinstein |
| 6,581,599 B1 | 6/2003 | Stenzler |
| 6,601,580 B1 | 8/2003 | Block et al. |
| 6,673,338 B1 | 1/2004 | Arnold et al. |
| 6,703,046 B2 | 3/2004 | Fitzhugh et al. |
| 6,706,274 B2 | 3/2004 | Herrmann et al. |
| 6,715,485 B1 | 4/2004 | Djupesland |
| 6,723,703 B2 * | 4/2004 | Gaston et al. ............. 514/1.8 |
| 6,747,062 B2 | 6/2004 | Murrell |
| 6,750,254 B2 | 6/2004 | Hrabie et al. |
| 6,758,214 B2 * | 7/2004 | Fine et al. ............. 128/203.12 |
| 6,780,849 B2 | 8/2004 | Herrmann et al. |
| 6,786,217 B2 | 9/2004 | Stenzler |
| 6,793,644 B2 | 9/2004 | Stenzler |
| 6,796,966 B2 | 9/2004 | Thomas |
| 6,811,965 B2 | 11/2004 | Vodovotz et al. |
| 6,867,194 B2 | 3/2005 | Wang et al. |
| 6,887,485 B2 | 5/2005 | Fitzhugh et al. |
| 6,911,478 B2 | 6/2005 | Hrabie et al. |
| 6,920,876 B2 | 7/2005 | Miller et al. |
| 6,938,357 B2 | 9/2005 | Hauch |
| 6,949,530 B2 | 9/2005 | Hrabie et al. |
| 7,048,951 B1 | 5/2006 | Seitz et al. |
| 7,105,502 B2 | 9/2006 | Arnold et al. |
| 7,118,767 B2 | 10/2006 | Kim et al. |
| 7,122,018 B2 | 10/2006 | Stenzler et al. |
| 7,199,154 B2 | 4/2007 | Berthelette et al. |
| 2002/0069877 A1 | 6/2002 | Villareal |
| 2002/0082566 A1 | 6/2002 | Stenzler |
| 2002/0119115 A1 | 8/2002 | Keefer et al. |
| 2002/0138051 A1 | 9/2002 | Hole et al. |
| 2002/0155164 A1 | 10/2002 | Figley et al. |
| 2002/0156416 A1 | 10/2002 | Stenzler |
| 2002/0169202 A1 | 11/2002 | Sakamoto et al. |
| 2003/0039697 A1 | 2/2003 | Zhao et al. |
| 2003/0131848 A1 * | 7/2003 | Stenzler ............. 128/204.18 |
| 2003/0150457 A1 | 8/2003 | Miller et al. |
| 2003/0165578 A1 | 9/2003 | Murrell |
| 2003/0203915 A1 | 10/2003 | Fang et al. |
| 2003/0215528 A1 | 11/2003 | Graham et al. |
| 2003/0228564 A1 | 12/2003 | Edrich et al. |
| 2004/0009238 A1 | 1/2004 | Miller et al. |
| 2004/0028753 A1 * | 2/2004 | Hedenstierna et al. ....... 424/718 |
| 2004/0043026 A1 | 3/2004 | Tuan et al. |
| 2004/0081580 A1 | 4/2004 | Hole et al. |
| 2004/0112378 A1 | 6/2004 | Djupesland |
| 2004/0131703 A1 | 7/2004 | Bach et al. |
| 2004/0163647 A1 | 8/2004 | Figley et al. |
| 2004/0180863 A1 | 9/2004 | Hrabie et al. |
| 2004/0259840 A1 | 12/2004 | Herrmann et al. |
| 2005/0016427 A1 | 1/2005 | Memory |
| 2005/0079148 A1 | 4/2005 | Fitzhugh et al. |
| 2005/0137521 A1 | 6/2005 | Stenzler |
| 2005/0142217 A1 | 6/2005 | Adams et al. |
| 2005/0148566 A1 | 7/2005 | Waterhouse et al. |
| 2005/0171066 A1 | 8/2005 | Shami |
| 2005/0191372 A1 | 9/2005 | Stenzler et al. |
| 2005/0217668 A1 | 10/2005 | Figley et al. |
| 2005/0217679 A1 | 10/2005 | Miller et al. |
| 2005/0251117 A1 | 11/2005 | Anderson et al. |
| 2005/0265958 A1 | 12/2005 | West et al. |
| 2005/0288260 A1 | 12/2005 | Hrabie et al. |
| 2006/0008529 A1 | 1/2006 | Meyerhoff et al. |
| 2006/0068031 A1 | 3/2006 | Miller et al. |
| 2006/0147553 A1 | 7/2006 | Miller et al. |
| 2007/0065473 A1 | 3/2007 | Miller et al. |
| 2007/0086954 A1 | 4/2007 | Miller et al. |
| 2007/0088316 A1 | 4/2007 | Stenzler et al. |
| 2007/0104653 A1 | 5/2007 | Miller et al. |

FOREIGN PATENT DOCUMENTS

| | | |
|---|---|---|
| EP | 0640357 A1 | 3/1995 |
| EP | 0659445 A1 | 6/1995 |
| EP | 0659445 B1 | 6/1995 |
| EP | 1243278 A2 | 9/2002 |
| FR | 2656218 | 6/1991 |
| JP | 3-139364 | 6/1991 |

| | | |
|---|---|---|
| JP | 3-207365 | 9/1991 |
| KR | 202066 | 6/1999 |
| WO | WO 92/17445 | 10/1992 |
| WO | WO 93/15779 | 8/1993 |
| WO | WO 93/17741 | 9/1993 |
| WO | WO 95/09612 | 4/1995 |
| WO | WO 96/00006 | 1/1996 |
| WO | WO 96/22803 | 8/1996 |
| WO | WO 96/25184 | 8/1996 |
| WO | WO 96/31217 | 10/1996 |
| WO | WO 98/01142 | 1/1998 |
| WO | WO 99/49921 | 10/1999 |
| WO | WO 00/07653 | 2/2000 |
| WO | WO 00/30659 | 6/2000 |
| WO | WO 01/65935 A1 | 9/2001 |
| WO | WO 02/056864 A2 | 7/2002 |
| WO | WO 03/066109 A1 | 8/2003 |
| WO | WO 2005/060603 A3 | 7/2005 |
| WO | WO 2005/110052 A3 | 11/2005 |
| WO | WO 2005/110441 A2 | 11/2005 |

OTHER PUBLICATIONS

Air Products MSDS nitric oxide Oct. 1998 6 pages.*
Nitric oxide MSDS(Joshua B. Halpern) Nov. 1995 12 pages.*
Tsukahara et al. (Nitric Oxide: Biology and Chemistry 1999, 3(3), 191-198).*
MSDS sodium azide Nov. 21, 2008 8 pages.*
Wang et al. Chem Rev 2002, 102, 1091-1134.*
Ratjen et al. (Respiratory Medicine 1999, 93, 579-583).*
Barnes (Annals of Medicine 1995, 27, 389-393).*
Ramnarine et al. (British J of Pharmacology 1996, 118, 998-1002).*
Mucolytics [online] retrieved on Apr. 26, 2013 from: http://www.patient.co.uk/health/mucolytics May 11, 2012; 16 pages.*
Yuta et al. Current Allergy and Asthma Reports 2005, 5, 243-251.*
Ray, James D. et al., "A New Method of Preparing Nitric Oxide," Contribution from the Department of Chemistry, Stanford University (1956).
Shank, J. L. et al., "The Effect of Nitric Oxide on Bacteria," Applied Microbio, No. 10, 189-189 (1962).
Norman, C. et al., "Nitrogen Oxides in Tobacco Smoke," Nature, vol. 205, No. 4971, pp. 915-916, (Feb. 1965).
Canetti, G., "Present aspects of bacterial resistance in tuberculosis," Am. Rev. Respir. Dis. 92:687-703 (1965).
Bass, H. et al., "Regional structure and function in brochiectasis," Am. Rev. Respir. Dis. 97:598-609 (1968).
Contractor, A. M. et al., "Development and Evaluation of an Inhalation Aerosol of Nitroglycerin," Journal of Pharmaceutical Sciences, vol. 63, No. 6, pp. 907-911 (Jun. 1974).
Oda, H. et al., "Nitrosyl-Hemoglobin Formation in the Blood of Animals Exposed to Nitric Oxide," Archives of Environmental Health, vol. 30, No. 7, pp. 453-456 (Sep. 1975).
Katsuki, S. et al., "Stimulation of Guanylate Cyclase by Sodium Nitroprusside, Nitroglycerin and Nitric Oxide in Various Tissue Preparations and Comparison to the Effects of Sodium Azide and Hydroxylamine." Journal of Cyclic Nucleotide Research, vol. 3, pp. 23-25 (1977).
Hugod, C., "Effect of exposure of 43 PPM nitric oxide and 3.6 PPM nitrogen dioxide on rabbit lung," Arch. Occup. Environ. Health 42:159-167 (1979).
Yoshida, J. et al., "Metabolic Fate of Nitric Oxide," Int Arch Occup Environ Health, vol. 46, No. 1, pp. 71-77 (Apr. 1980).
Borland, C., "The Fate of Inhaled Nitric Oxide," Clinical Science, Abstract No. 104, p. 37P (1983).
Mancinelli et al., "Effects of Nitric Oxide and Nitrogen Dioxide on Bacterial Growth," Applied and Environmental Microbiology, vol. 46, No. 1, pp. 198-202 (Jul. 1983).
Demling, R. H. et al., "The Pulmonary and Systemic Response to Recurrent Endotoxemia in the Adult Sheep," Surgery, vol. 100, No. 5, pp. 876-883 (Nov. 1986).
Higenbottam, T., "Primary Pulmonary Hypertension," British Medical Journal, vol. 293, pp. 1456-1457 (Dec. 1986).
Higenbottam, T. et al., "Primary Pulmonary Hypertension," British Medical Journal, vol. 294, p. 705 (Mar. 1987).
Palmer, R.M.J. et al., "Nitric Oxide Release Accounts for the Biological Activity of Endothelium-Derived Relaxing Factor," Nature, vol. 327, pp. 524-526 (Jun. 1987).
Ignarro, L. J. et al., "Endothelium-Derived Relaxing Factor Produced and Released From Artery and Vein is Nitric Oxide," Proceedings of the National Academy of Sciences of the United States of America, vol. 84, No. 24, pp. 9265-9269 (Dec. 1987).
Higenbottam, T. W. et al., "Inhaled 'Endothelium Derived-Relaxing Factor' (EDRF) in Primary Hypertension (PPH)," Abstract, American Review of Respiratory Disease, Suppl., vol. 137, No. 4, Part 2, p. 107 (Apr. 1988).
Ignarro, L. J. et al., "Endothelium-Derived Relaxing Factor and Nitric Oxide Possess Identical Pharmacologic Properties as Relaxants of Bovine Arterial and Venous Smooth Muscle," The Journal of Pharmacology and Experimental Therapeutics, vol. 246, No. 1, pp.
Dinh-Xuan, A. T. et al., "Non-Prostanoid Endothelium-Derived Vasoactive Factors," The Journal of International Medical Research, vol. 17, pp. 305-315 (1989).
Borland, C. D. R. et al., "A Simultaneous Single Breath Measurement of Pulmonary Diffusing Capacity with Nitric Oxide and Carbon Monoxide," The European Respiratory Journal, vol. 2, No. 1, pp. 56-63 (Jan. 1989).
Buga, G. M. et al., "Endothelium-Derived Nitric Oxide Relaxes Nonvascular Smooth Muscle," European Journal of Pharmacology, vol. 161, No. 1, pp. 61-72, (Feb. 1989).
Garg, U. C. et al., "Nitric Oxide-generating Vasodilators and 8-Bromo-Cyclic Guanosine Monophosphate Inhibit Mitogensis and Proliferation of Cultured Rat Vascular Smooth Muscle Cells," The Journal of Clinical Investigation, vol. 83, No. 5, pp. 1774-1777 (May 1989).
Meyer, M. et al., "Nitric Oxide (NO), a New Test Gas for Study of Alveolar-capillary Diffusion," The European Respiratory Journal, vol. 2, No. 6, pp. 494-496 (Jun. 1989).
Dinh-Xuan, A. T. et al., "Primary Pulmonary Hypertension: Diagnosis, Medical and Surgical Treatment," vol. 84, pp. 189-197 (1990).
Stavert, D. M. et al., "Nitric Oxide and Nitrogen Dioxide as Inducers of Acute Pulmonary Injury When Inhaled at Relatively High Concentrations for Brief Periods," Inhalation Toxicology 2:53-67 (1990).
Moinard, J. et al., "Determination of Lung Capillary Blood Volume and Membrane Diffusing capacity in Patients with COLD using the NO-CO Method," The European Respiratory Journal, vol. 3, pp. 318-322 (1990).
Archer, S. L., "Comparison of the Hemodynamic Effects of Nitric Oxide and Endothelium-Dependent Vasodilators in Intact Lungs," Journal of Applied Physiology, vol. 68, No. 2, pp. 735-747 (Feb. 1990).
Meyer, M. et al., "Pulmonary Diffusing Capacities for Nitric Oxide and carbon Monoxide Determined by Rebreathing in Dogs," Journal of Applied Physiology, vol. 68, No. 6, pp. 2344-2357 (Jun. 1990).
Vane, J. R. et al., "Regulatory Functions of the Vascular Endothelium," The New England Journal of Medicine, vol. 323, No. 1, pp. 27-36 (Jul. 1990).
Higenbottam, T. et al., "Has the Treatment of Asthma Improved?" Chest, vol. 98, No. 3, pp. 706-712 (Sep. 1990).
Swami, A. et al., "The Pulmonary Physician and critical Care: 2. The Injury Lung: Conventional and Novel Respiratory Therapy," Thorax, vol. 47, pp. 555-562 (1992).
Bult, H. et al., "Chronic Exposure to Exogenous Nitric Oxide May Suppress its Endogenous Release and Efficacy," Journal of Cardiovascular Pharmacology, vol. 17, Suppl. 3, pp. S79-S82 (1991).
Frostell, C. et al., "Inhaled Nitric Oxide, A Selective Pulmonary Vasodilator Reversing Hypoxic Pulmonary Vasoconstriction," Circulation Journal of the American Heart Association, vol. 83, pp. 2083-2047 (1991).
Hendrickson, D.A. et al, "Regents and Stains," Manual of Clinical Microbiology, 5th Ed., American Society for Microbiology, pp. 1289-1314 (1991).
Cremona, g. et al., "Endothelium-derived Relaxing Factor and the Pulmonary Circulation," Lung, vol. 169, pp. 185-202 (1991).
Falke, K. et al., "Inhaled Nitric Oxide Selectively Reduces Pulmonary Hypertension in Severe ARDS and Improves Gas Exchange as well as right Heart Ejection fraction—A Case Report," Abstract 248, Am. Rev. Respir. Dis., vol. 143 (1991).

Fratacci, M. D., "Inhaled Nitric Oxide—A Selective Pulmonary Vasodilator of Heparin-Protamine Vasoconstriction in Sheep," Anesthesiology, vol. 75, pp. 990-999 (1991).
Denis, M., "Interferon—Gamma-treated Murine Macrophages Inhibit Growth of Tubercle Bacilli via the Generation of Reactive Nitrogen Intermediates," Cellular Immunology, vol. 132, No. 1, pp. 150-157 (Jan. 1991).
Dinh-Xuan, A. T. et al., "Impairment of Endothelium-Dependent Pulmonary-Artery Relaxation in Chronic Obstructive Lung Disease," The New England Journal of Medicine, vol. 324, No. 22, pp. 1539-1547 (May 1991).
Frostell, C. et al., "Inhaled Nitric Oxide—A Selective Pulmonary Vasodilator Reversing Hypoxic Pulmonary Vasoconstriction," Circulation, vol. 83, No. 6 (Jun. 1991).
Moncada, S. et al., "Nitric Oxide: Physiology, Pathophysiology, and Pharmacology," Pharmacological Reviews, vol. 43, No. 2 (Jun. 1991).
Frostell, C. et al., "Inhaled Nitric Oxide Dilates Human Hypoxic Pulmonary Vasoconstriction Without Causing Systemic Vasodilation," Anesthesiology, The Journal of the American Society of Anesthesiologists, Inc., vol. 75, No. 3A, Abstract A989 (Sep. 1991).
Girard, C. et al., "Inhaled Nitric Oxide (NO) in Pulmonary Hypertension Following Mitral Valve Replacement," Anesthesiology, The Journal of The American Society of Anesthesiologists, Inc., vol. 75, No. 3A, Abstract A983 (Sep. 1991).
Roberts, J. D. et al., "Inhaled Nitric Oxide (NO): A Selective Pulmonary Vasodilator for the Treatment of Persistent Pulmonary Hypertension of the Newborn (PPHN)," Abstract 1279, Circulation, vol. 84, No. 4, p. ii-321 (Oct. 1991).
Pepke-Zaba, J. et al., "Inhaled Nitric Oxide as a Cause of Selective Pulmonary Vasodilatation in Pulmonary Hypertension," The Lancet, vol. 338, No. 8776, pp. 1173-1174 (Nov. 1991)
Radomski, M. W., et al., "Human Colorectal Adenocarcinoma Cells: Differential Nitric Oxide Synthesis Determines Their Ability to Aggregate Platelets," Cancer Research, vol. 51, pp. 6073-6078 (Nov. 15, 1991).
Johns, R. A., "EDRF/Nitric Oxide—The Endogenous Nitrovasodilator and a New cellular Messenger," Anesthesiology, The Journal of the American Society of Anesthesiologists, Inc., vol. 75, No. 6, pp. 927-931 (Dec. 1991).
Pearl, R. G., "The Pulmonary Circulation," Anesthesiology, vol. 5, pp. 848-854 (1992).
Chan, J. et al., "Killing of Virulent *Mycobacterium tuberculosis* by Reactive Nitrogen Intermediates Produced by Activated Murine Macophages," J. Exp. Med. 175:1111-1122 (Apr. 1992).
Rossiant, R. et al., "Successful Treatment of Severe Adult Respiratory Distress Syndrome with Inhaled Nitric Oxide," American Review of Respiratory Disease, Suppl., vol. 145, No. 4, Part 2, p. A80 (Apr. 1992).
Rossiant, R. et al., "Inhaled Nitric Oxide in Contrast to Infused Prostacyclin Selectively Reduces Pulmonary Hypertension and Improves Gas Exchange in Severe ARDS," Abstract, American Review of Respiratory Disease, Suppl., vol. 145, No. 4, Part 2, p. A185.
Bigatello, L. M., "Inhaled Nitric Oxide is a Selective Pulmonary Vasodilator in Septic Patients with Severe ARDS," Abstract, American Review of Respiratory Disease, Suppl., vol. 145, No. 4, Part 2, p. A185 (Apr. 1992).
Snyder, S. H. et al., Biological Roles of Nitric Oxide, Scientific American, vol. 266, No. 5, pp. 68-77 (May 1992).
Foubert, L., "Safety Guidelines for Use of Nitric Oxide," The Lancet, vol. 339, No. 8809, pp. 1615-1616 (Jun. 1992).
Messent, M. et al., "Pharmacotherapy in Lung Injury," Thorax, vol. 47, No. 7, pp. 651-656 (Jul. 1992).
Barash, P. et al., "Anesthesiology," The Journal of the American Medical Association, vol. 268, No. 3, pp. 335-337 (Jul. 1992).
Dupuy, P. M. et al., "Bronchodilator Action of Inhaled Nitric Oxide in Guinea Pigs," J. Clin. Invest., vol. 90, pp. 421-428 (Aug. 1992).
Kinsella, J. P. et al., "Hemodynamic Effects of Exogenous Nitric Oxide in Ovine Transitional Pulmonary Circulation," American Journal of Physiology: Heart and Circulatory Physiology, vol. 32, No. 3, pp. H875-H880 (Sep. 1992).

Roberts, J. D. et al., "Inhaled Nitric Oxide in Persistent Pulmonary Hypertension of the Newborn," The Lancet, vol. 340, pp. 818-819 (Oct. 1992).
Kinsella, J. P. et al., "Low-Dose Inhalational Nitric Oxide in Persistent Pulmonary Hypertension of the Newborn," The Lancet, vol. 340, pp. 819-820 (Oct. 1992).
Girard, C. et al., "Inhaled Nitric Oxide After Mitral Valve Replacement in Patients with Chronic Pulmonary Artery Hypertension," Anesthesiology, The Journal of the American Society of Anesthesiologists, Inc., vol. 77, No. 5, pp. 880-883 (Nov. 1992).
Kacmarek, R. M., "Nitric Oxide as a Bronchodilator in Methacholine Induced Bronchospasm in Mild Asthmatics," Abstract (1993).
Blomqvist, H. et al., "Enhanced Pneumonia Resolution by Inhalation of Nitric Oxide?" Acta Anaesthesiol Scand, vol. 37, pp. 110-114 (1993).
Buga, G. M. et al., "Negative Feedback Regulation of Endothelial Cell Function by Nitric Oxide," Circulation Research, Journal of the American Heart Association, 73:808-812 (1993).
Higenbottam, T., "Inhaled Nitric Oxide: A Magic Bullet?" Quarterly Journal of Medicine, vol. 86, pp. 555-558 (1993).
Stenqvist, O. et al., "Evaluation of a New System for Ventilatory Administration of Nitric Oxide," Acta Anaesthesiologica Scandinavica, pp. 687-691 (1993).
Rossaint, R. et al., "Inhaled Nitric Oxide for the Adult Respiratory Distress Syndrome," New England Journal of Medicine, vol. 328, pp. 399-405 (Feb. 1993).
Maragos, C. M., et al., "Nitric Oxide/Nucleophile Complexes Inhibit the in Vitro Proliferation of A375 Melanoma Cells via Nitric Oxide Release," Cancer Research, vol. 53, pp. 564-568 (Feb. 1, 1993).
Pearl, R. G., "Inhaled Nitric Oxide—The Past, The Present and the Future," Anesthesiology, vol. 78, No. 3, pp. 413-416 (Mar. 1993).
Assreuy, J. et al., "Feedback Inhibition of Nitric Oxide Synthase Activity by Nitric Oxide," British Journal of Pharmacology, vol. 108, pp. 883-837 (Mar. 1993).
Higenbottam, T. et al., "Highlights on Pulmonary Hypertension: A Commentary," The European Respiratory Journal, vol. 6, No. 7, pp. 932-933 (Jul. 1993).
Haworth, S. G., "Pulmonary Hypertension in Childhood," The European Respiratory Journal, vol. 6, No. 7, pp. 1037-1043 (Jul. 1993).
Higenbottam, T. et al., "Acute and Chronic Hypoxic Pulmonary Hypertension," The European Respiratory Journal, vol. 6, No. 8, pp. 1207-1212 (Sep. 1993).
Mansch, R. et al., "Simulation of Microbiologically and chemically Influenced corrosion of Natural Sandstone," Abstract, ASTM Special Technical Publication, 203-16; 1 pg. (1994).
Lowenstein, C. J. et al., "Nitric Oxide: a Physiologic Messenger," Annals of Internal Medicine, vol. 120, Issue 3, pp. 227-237 (Feb. 1994).
Dong, Z., et al., "Inverse Correlation Between Expression of Inducible Nitric Oxide Synthase Activity and Production of Metastasis in K-1735 Murine Melanoma Cells," Cancer Research, vol. 54, pp. 789-793 (Feb. 1, 1994).
Butt, A. Y. et al., "New Therapies for Primary Pulmonary Hypertension," Chest, vol. 105, No. 2, pp. 21S-25S (Feb. 1994).
Foubert, L. et al., "Nitric Oxide in Pulmonary Hypertension: Therapeutic Considerations," Journal of Cardiothoracic and Vascular Anesthesia, vol. 8, No. 3, Suppl. 2, p. 41 (Jun. 1994).
Snow, D. et al., "Inhaled Nitric Oxide in Pulmonary Hypertension," Journal of Cardiothoracic and Vascular Anesthesia, vol. 8, No. 3, Suppl. 2, Abstract No. 127 (Jun. 1994).
O'Brien, L. et al., Strains of *Mycobacterium tuberculosis* Differ in Susceptibility to Reactive Nitrogen Intermediates in Vitro, Infection and Immunity, vol. 62, No. 11, pp. 5187-5190 (Aug. 1994).
Young, J. D., "A Universal Nitric Oxide Delivery System," British Journal of Anaesthesia, vol. 73, No. 4, pp. 700-702 (Oct. 1994).
Hagenah, Jens-Uwe, "The Use of Nitric Oxide (NO) in Intensive Care Ventilation," Dragerwerk Aktiengesellscha, pp. 1 and 3-36.
Hanson, S. R., et al., "Nitric Oxide Donors: A Continuing Opportunity in Drug Design," Nitric Oxide Biochemistry, Molecular Biology, and Therapeutic Implications, Advances in Pharmacology, vol. 34, pp. 383-398 (1995).

Chan, J. et al., "Effects of Nitric Oxide Synthase Inhibitors on Murine Infection with *Mycobacterium tuberculosis*," Infection and Immunity, vol. 63, No. 2, pp. 736-740 (Feb. 1995).

DeGroote, M. A., et al., "NO Inhibitions: Antimicrobial Properties of Nitric Oxide," Clinical Infectious Diseases, vol. 21, Suppl. 2, pp. S162-S165 (Oct. 1995).

Body, S. C., M.D. et al., "Nitric Oxide: Delivery, Measurement, and Clinical Application," Journal of Cardiothoracic and Vascular Anesthesia, vol. 9, No. 6, pp. 748-763 (Dec. 1995).

Higenbottam, T. et al., "The Treatment of Primary Pulmonary Hypertension," Therapeutic Applications of Iloprost, A Volume in the Clinical Monograph Series, pp. 35-41 (Apr. 1995).

Szabo, C., "The Pathophysiological Role of Peroxynitrite in Shock, Inflammation and Ischemia-Reperfusion Injury," Shock, vol. 6, No. 2, pp. 79-88 (1996).

Higenbottam, T., "Nitric Oxide and the Lung," Horizons in Medicine, No. 7 pp. 203-224 (1996).

Young, J. D. et al., "Delivery and Monitoring of Inhaled Nitric Oxide," Intensive Care Medicine, vol. 22, No. 1, pp. 77-86 (Jan. 1996).

Mellgren, K., et al., "Nitric Oxide in the Oxygenator Sweep Gas Reduces Platelet Activation During Experimental Perfusion," The Annals of Thoracic Surgery, vol. 61, No. 4, pp. 1194-1198 (Apr. 1996).

Ramnarine, S. I., et al., "Nitric Oxide Inhibition of Basal and Neurogenic Mucus Secretion in Feerrete Trachea in Vitro," British Journal of Pharmacology, vol. 118 (4), pp. 998-1002 (Jun. 1996).

Channick, R. N., M.D. et al., "Pulsed Delivery of Inhaled Nitric Oxide to Patients with Primary Pulmonary Hypertension," Chest, The Cardiopulmonary and Critical Care Journal, vol. 109, No. 6, pp. 1545-1549 (Jun. 1996).

Hudome, S. M., M.D. et al., "Precise Control of Nitric Oxide Concentration in the Inspired Gas of Continuous Flow Respiratory Devices," Pediatric Pulmonology, vol. 22, No. 3, pp. 182-187 (Sep. 1996).

Cuthbertson, B. H. et al., "Inhaled Nitric Oxide," The Lancet, vol. 348, No. 9039, pp. 1447-1448 (Nov. 1996).

Gerlach, H. et al., "Low Levels of Inhaled Nitric Oxide in Acute Lung Injury," Nitric Oxide and the Lung, vol. 98, Chapter 14, pp. 271-283 (1997).

Dupuy, P. M. et al., "Bronchial Effects of Nitric Oxide," Nitric Oxide and the Lung, vol. 98, Chapter 15, pp. 285-311 (1997).

Leopold, J. A. et al., "New Developments in Nitrosovasodilator Therapy," Vascular Medicine, vol. 2, No. 3 (1997).

Rook, G. A. W., "Intractable Mycobacterial Infections Associated with Genetic Defects in the Receptor for Interferon Gamma: What Does This Tell Us About Immunity to Mycobacteria?" Thorax, vol. 52 (Suppl. 3), pp. S41-S46 (1997).

Katayama, Y. et al., "Inhaled Nitric Oxide and Arterial Oxygen Tension in Patients with chronic Obstructive Pulmonary Disease and Severe Pulmonary Hypertension," Thorax, The Journal of the British Thoracic Society, vol. 52, pp. 120-124 (1997).

Neonatal Inhaled Nitric Oxide Study Group, "Inhaled Nitric Oxide in Full-Term and Nearly Full-Term Infants with Hypoxic Respiratory Failure," New England Journal of Medicine, 336(9):597-604 (Feb. 1997).

Roberts, J. D. et al., "Inhaled Nitric Oxide and Persistent Pulmonary Hypertension of the Newborn," New England Journal of Medicine, 336:605-610 (Feb. 1997).

Imanaka, H., M.D. et al., "Inaccuracies of Nitric Oxide Delivery Systems During Adult Mechanical Ventilation," Anesthesiology, vol. 86, No. 3, pp. 676-688 (Mar. 1997).

Marriott, H. et al., "The Role of Nitric Oxide in Respiratory Disease," Schweiz Med Wochenschr, vol. 127, pp. 709-714 (Apr. 1997).

Nozaki, Y. et al., "Mechanism of Nitric Oxide-Dependent Killing of *Mycobacterium bovis* BCG in Human Alveolar Macrophages," Infection and Immunity, vol. 65, pp. 3644-3647 (Sep. 1997).

Hess, D., RRT, Ph.D. et al., "Delivery Systems for Inhaled Nitric Oxide," Respiratory Care Clinics of North America, vol. 3, No. 3, pp. 371-410 (Sep. 1997).

Hoehn T., M.D. et al., "Effect of Therapeutic Concentrations of Nitric Oxide on Bacterial Grown in Vitro," Crit Care Med, vol. 26, No. 11, pp. 1857-1862 (1998).

Bauer, J. A. et al., Evaluation of Linear Polyethylenei-mine/Nitric Oxide Adduct on Wound Repair: Therapy Versus Toxicity, The Wound Healing Society, pp. 569-577 (1998).

Pizzichini, M. M. M. et al., "Asthma and Natural Colds: Inflammatory Indices in Induced Sputum: A Feasibility Study," American Journal of Respiratory Critical Care Medicine, vol. 158, pp. 1178-1184 (1998).

Higenbottam, T. et al., "Primary and Secondary Pulmonary Hypertension," Seminars in Respiratory and Critical Care Medicine, vol. 19, No. 1, pp. 91-95 (1998).

Long R. et al., "Pulmonary Tuberculosis Treated with Directly Observed Therapy: Serial Changes in Lung Structure and Function," Chest, vol. 113, pp. 933-943 (1998).

Klein, M.D. et al., "Nitric Oxide Delivery Systems," Acta Anaesthesiologica Scandinavica, pp. 274-275 (1998).

Francoe, M, RRT et al., "Inhaled Nitric Oxide: Technical Aspects of Administration and Monitoring," Critical Care Medicine, vol. 26, No. 4, pp. 782-796 (Apr. 1998).

Keefer, L. K., "Nitric Oxide-Releasing Compounds: From Basic Research to Promising Drugs," The American Chemical Society, vol. 28, pp. 30-35 (Aug. 1998).

Ivy, D. D., M.D. et al., "Acute Hemodynamic Effects of Pulsed Delivery of Low Flow Nasal Nitric Oxide in Children with Pulmonary Hypertension," The Journal of Pediatrics, vol. 133, No. 3, pp. 453-456 (Sep. 1998).

Hiesmayr, M. J. et al., "Performance of Proportional and Continuous Nitric Oxide Delivery Systems During Pressure- and Volume-Controlled Ventilation," The British Journal of Anaesthesia, vol. 81, No. 4, pp. 544-552 (Oct. 1998).

Katayama, Y., M.D. et al., "Minimizing the Inhaled Dose of NO With Breath-by-Breath Delivery of Spikes of Concentrated Gas," Circulation, Journal of the American Heart Association, vol. 98, No. 22 (Dec. 1998).

Higenbottam, T. et al., "Treatments for Severe Pulmonary Hypertension," The Lancet, vol. 353, No. 9150, pp. 338-340 (Jan. 1999).

Long, R. et al., "Mycobacteriocidal Action of Exogenous Nitric Oxide," Antimicrobial Agents and Chemotherapy, vol. 43, No. 2, pp. 403-405, (Feb. 1999).

Schofnagl, H. et al., "Proportional and Continuous NO Delivery Systems," British Journal of Anaesthesia, vol. 82, No. 4, pp. 647-653 (Apr. 1999).

Rimmelzwaan, G. F. et al., "Inhibition of Influenza Virus Replication by Nitric Oxide," Journal of Virology, American Society for Microbiology, vol. 73, No. 10, pp. 8880-8883 (Oct. 1999).

Webert, K. E., M.D. et al., "Effects of Inhaled Nitric Oxide in a Rat Model of *Pseudomonas ceruginosa* Pneumonia," Crit Car Med, vol. 28, No. 7, pp. 2397-2405 (2000).

Tamaoki, J., M.D., et al., "Impairment of Airway Mucociliary Transport in Patients with Sinobronchial Syndrome: Role of Nitric Oxide," Journal of Aerosol Medicine, vol. 13, No. 3, pp. 239-244 (Nov. 2000).

Long et al., "Treatment of Sputum-Smear Positive Pulmonary Tuberculosis With Inhaled Nitric Oxide," 2001-Abstract Form to the ATS 2001 San Francisco, May 18-23, 2001 (faxed Mar. 27, 2001).

Frank, S., et al., "Nitric Oxide Drives Skin Repair: Novel Functions of an Established Mediator," Kidney International, vol. 61, pp. 882-888 (2002).

Imada, M., et al., "Functional Roles of Nasal Nitric Oxide in Nasal Patency and Mucociliary Function," ACTA Oto-Laryngologica, vol. 122, No. 5, pp. 513-519 (Jul. 2002).

Kirov, M. Y., M.D., et al., "Combination of Intravenously Infused Methylene Blue and Inhaled Nitric Oxide Ameliorates Endotoxin-Induced Lung Injury in Awake Sheep," Critical Care Medicine, vol. 31, No. 1, pp. 179-186 (Jan. 2003).

Shami, P. J., et al., JS-K, A Glutathione/Glutathione S-Transferase-activated Nitric Oxide Donor of the Diazeniumdiolate Class with Potent Antineoplastic Activity, Molecular Cancer Therapeutics, vol. 2, pp. 409-417 (Apr. 2003).

Counter-Defendant's First Amended Responses to Counterclaimant's Second Set of Interrogatories Relating to Counterclaims (Nos. 19-38) (Oct. 2003).

Miller, Chris C. et al.; "Treatment of Chronic Nonhealing Leg Ulceration with Gaseous Nitric Oxide: A Case Study"; Journal of Cutaneous Medicine and Surgery, pp. 233-238 (2004).

Vijh, A. K., "High Infectious Burden, Low Cancer Incidence, and Early Malignancy in Developing Countries: A Molecular Hypothesis in Term of the Role of Nitric Oxide," Medical Hypotheses, vol. 63, pp. 208-210 (Feb. 2004).

Sanders, S. P. et al., "Role of Nasal Nitric Oxide in the Resolution of Experimental Rhinovirus Infection," Journal of Allergy and Clinical Immunology, vol. 113, No. 4, pp. 697-702 (Apr. 2004).

Schmidt, I. et al., Physiologic and Proteomic Evidence for a Role of Nitric Oxide in Biofilm Formation by *Nitrosomonas europaea* and Other Ammonia Oxidizers; Journal of Bacteriology, vol. 186, No. 9, pp. 2781-2788 (May 2004).

Reynolds, M. M., et al., "Nitric Oxide-Releasing Hydrophobic Polymers: Preparation, Characterization, and Potential Biomedical Applications," Free Radical Biology & Medicine, The Official Journal for the Society for Free Radical Biology and Medicine, vol. 37, No. 7, pp. 926-936 (Oct. 2004).

Lechner, M., et al., "Inducible Nitric Oxide Synthase (iNOS) in Tumor Biology: The Two Sides of the Same Coin," Seminars in Cancer Biology, vol. 15, pp. 277-289 (2005).

Ghaffair, A., et al., "A Direct Nitric Oxide Gas Delivery System for Bacterial and Mammalian Cell Cultures," Nitric Oxide Biology and Chemistry, vol. 12, pp. 129-140 (2005).

Proud, D., "Nitric Oxide and the Common Cold," Journal of Allergy and Clinical Immunology, vol. 5, pp. 37-42 (2005).

Nablo, B. J., et al., Inhibition of Implant-Associated Infections Via Nitric Oxide Release, Science Direct, Biomaterials, vol. 26, pp. 6984-6990 (May 2005).

McMullin, B. B., MSc RRT, et al., "The Antimicrobial Effect of Nitric Oxide on the Bacteria That Cause Nosocomial Pneumonia in Mechanically Ventilated Patients in the Intensive Care Unit," Respiratory Care, vol. 50, No. 11, pp. 1451-1456 (Nov. 2005).

Hurford, W. E.; Nitric Oxide As a Bacterial Agent: Is the Cure Worse Than the Disease?; Respiratory Care, vol. 50, No. 11, pp. 1428-1429 (Nov. 2005).

Katayama, Y. et al., "A Minimal Dose of Inhaled Nitric Oxide Delivered As a 'Spike' of Small Volume in Early Inhalation," Section of Respiratory Medicine, Division of Clinical Sciences, The Medical School, University of Sheffield (23 pages).

Turchi, J. J., "Nitric Oxide and Cisplatin Resistance: NO Easy Answers," PNAS, vol. 103, No. 12, pp. 4337-4338 (Mar. 21, 2006).

\* cited by examiner

USE OF INHALED GASEOUS NITRIC OXIDE AS A MUCOLYTIC AGENT OR EXPECTORANT

CLAIM OF PRIORITY

This application claims priority to and is a continuation in part application of PCT Application No. PCT/US2005/016428 filed on May 11, 2005, which claims priority to Provisional Patent Application Ser. No. 60/569,888 filed on May 11, 2004, which are herein expressly incorporated by reference.

FIELD OF THE INVENTION

The field of the present invention relates to methods and systems for treating, preventing, or mitigating mucus accumulation and mucociliary dyskinesia in the airways of mammals, and in particular, to the inhaled use of gaseous Nitric Oxide (gNO) for mucolysis.

BACKGROUND OF THE INVENTION

Mucus is comprised of high molecular weight proteins. It is a heterogeneous mix of primarily water, electrolytes, lipids, and proteins in a gel matrix. Goblet cells and submucosal glands that are located along the tracheobronchial tree produce it. Mucus is secreted in response to irritation of the airways and is elicited by viral, bacterial, and of major import, environmental contamination, primarily small particulates and allergens.

Airway hygiene and integrity also depends on mucociliary clearance (MCC), which in turn depends upon the movement of viscoelastic mucus along the tracheobronchial tree by the beating of the ciliary appendages of airway epithelial cells. However, because mucus secretions are viscous and thick, it is difficult for the ciliary appendages to move them, and excess accumulation further burdens the mucociliary functions. Conditions that encumber MCC result in an inflammatory response to the airway and increase the risk of colonization by microorganisms, such as pathogens, which if chronic, up regulate mucus production. Encumbered MCC may thus result in a vicious cycle of inflammatory damage with the potential for future damage to both the upper and lower airway. See e.g., Cole P., Minerva Anestesiol. 2001 April; 67(4): 206-9, "Pathophysiology and treatment of airway mucociliary clearance. A moving tale." Additionally, mucociliary dyskinesia, a condition of impaired mucociliary movement in the airways, is derived from a number of similar vectors, including environmental, and likewise result in impaired mucociliary clearance times of respiratory secretions. See e.g., Pedersen M. Lung. 1990; 168 Suppl: 368-76, "Ciliary Activity and Pollution." Of note is the role of nitric oxide in secondary ciliary dyskensia found in inflammatory disorders of the respiratory tract.

In equine mammals, for example, excessive mucus accumulation and the resulting inflammation prevalence may be present in as great as 33% of the population. Inflamed airways resulting from viral, bacterial, or environmental vectors result in excess mucus residence. Excessive mucus accumulation is a significant risk factor for poor performance in racehorses. See e.g., S. J. Holcombe, N. E. Robinson, F. J. Derksen, et. al. 50th Annual Convention of the American Association of Equine Practitioners, 2004 (www.ivis.org), 4 Dec. 2004; P1441.1204, "Trachea Mucus Is Associated With Poor racing Performance In Thoroughbred Horses."

Furthermore, excessive mucus accumulation often manifests into Inflammatory Airway Disease (IAD). In humans, mucus accumulation also accompanies several respiratory diseases and conditions, such as acute bronchitis, chronic pulmonary disease, Bronchiectasis and Cystic Fibrosis.

Attempts at treating these airway derangements have focused on a wide range of interventions (antimicrobials, mucolytics, etc.) with limited success, particularly as it applies to the performance horse. Thus, there exists a need for more effective treatment methods for treating and preventing excess mucus accumulation and related pathology.

SUMMARY OF INVENTION

The Applicants have unexpectedly found that gaseous NO when inhaled is an effective mucolytic agent that can break down thick mucus aiding in mucociliary clearance in the respiratory tract of mammals. Using an equine model as an example, the Applicants have demonstrated that the administration through inhalation of nitric oxide containing gas is an effective treatment of mucus accumulation, including the treatment of secondary mucociliary dyskinesia via increased mucociliary clearance in mammals. By breaking down the mucus to a less viscous liquid, mucociliary clearance is increased. Additionally, the administration of gNO further protects the respiratory airways from the vicious cycle of inflammatory damage and colonization by microbes because of its anti-infective activity. Thus, gaseous nitric oxide (gNO) can be administered by inhalation as a novel methodology for reducing the severity and pathology of excess mucus residence in a mammal's respiratory airway, and in particular as an mucolytic agent or expectorant.

In one aspect of the present invention, mammals exhibiting excess mucus accumulation are identified and diagnosed. A source of gNO is provided, preferably in a pressurized cylinder coupled to flow control valves and pressure regulators. gNO may also be diluted with other gases such as $N_2$, air, or $O_2$ to form a nitric oxide containing gas at a therapeutically effective amount of nitric oxide sufficient to reduce the presence of mucus in the mammal's airways by at least about 20%, preferably by at least about 50%, and more preferably by about at least about 75%. The nitric oxide containing gas is administered to the mammal, preferably through nasal delivery, but may also include oral delivery, for example, through a face mask or an endotracheal tube.

Preferably, the flow rate of gaseous nitric oxide is regulated dependent on the mammal's respiratory tidal volume and the administration is repeated over several breaths. The target concentration of nitric oxide in the mammal's airways preferably ranges from 80 ppm to 400 ppm, and more preferably 160 ppm to 220 ppm. The administration of the inhaled nitric oxide containing gas may also coincide with a synchronous parameter of the mammal's respiratory cycle.

Another aspect of the present invention includes prevention of excess mucus accumulation in a mammal's airway. Mammals that are at risk of excess mucus accumulation may be identified and diagnosed. Therapeutic effective concentration of nitric oxide may then be nasally or orally administered in an amount sufficient to prevent excess mucus accumulation, inflammation, and eventually colonization by microbes.

In another aspect of the invention, apparatuses and systems for treating or preventing excess mucus accumulation in a mammal's airway are provided. For example, the system may comprise an endoscope for determining an amount of mucus accumulation in a mammal's airway using a scoring system such as a discrete scale of 0 to 5, representing the absence of mucus to high levels of mucus, respectively. A nitric oxide delivery device may be provided that include a source of nitric oxide containing gas, preferably from a pressurized source of gaseous NO such as a canister or cylinder, and a delivery interface for interfacing with the mammal's mouth or nares. The nitric oxide delivery device is preferably controlled by a control unit such as a microprocessor-based computer or analog controller wherein, depending on the scoring input representing the level of mucus accumulation, a distinct gNO therapeutic profile is selected and delivered to the mammals. Such therapeutic profile may be pre-determined or may be programmed by the user. The control unit then controls a flow meter and/or a control valve that regulates the flow of nitric oxide containing gas, either diluted or flowing directly from the pressurized source of gaseous NO.

Preferably, the apparatus delivers a quantity of the nitric oxide containing gas by regulating the flow rate depending on the mammal's respiratory tidal volume for a selected number of breaths at a certain concentration for the inputted score.

In another aspect of the invention, a system for treating mucus accumulation and/or mucociliary dyskenesia is provided. The system may comprise a pressurized source (e.g., canister or cylinder) of nitric oxide containing gas and a visible label affixed to the container, wherein the label indicates that the nitric oxide containing gas is suitable as a mucolytic agent or expectorant for reducing mucus accumulation and/or treating mucociliary dyskenesia in a mammal's airway. The system may further comprise instructions for delivery of the nitric oxide containing gas and/or instructions for therapeutic amounts or dosages of nitric oxide. Preferably, the concentration of nitric oxide in the pressurized source ranges from about 160 ppm to about 400 ppm, but may also be in excess of that amount such as 800 ppm to 10,000 ppm that may need to be diluted with other gases before use.

In a preferred embodiment, the pressurized source of nitric oxide containing gas is portable and can be carried by the mammal prior or by the animal's handler to initiation of treatment. The pressurized source may also include a release valve for controllably releasing the nitric oxide containing gas into a channel, tube or nozzle adaptable to direct the nitric oxide containing gas to a nostril or mouth of the mammal. The release valve can be actuated to release the nitric oxide containing gas.

In another aspect of the invention, administration of NO-releasing compounds, donors or upregulators is an effective treatment of mucus accumulation, including the treatment of secondary mucociliary dyskensia via increased mucociliary clearance in mammals. By breaking down the mucus to a less viscous liquid, mucociliary clearance is increased. NO-releasing compounds, NO-donors or NO-upregulators can be administered in any one, or a combination, of the following routes: intravenous injection, intraarterial injection, transcutaneous delivery, oral delivery, and inhalation (e.g. of a gas, powder, or liquid).

DETAILED DESCRIPTION OF THE INVENTION

Figure 1:
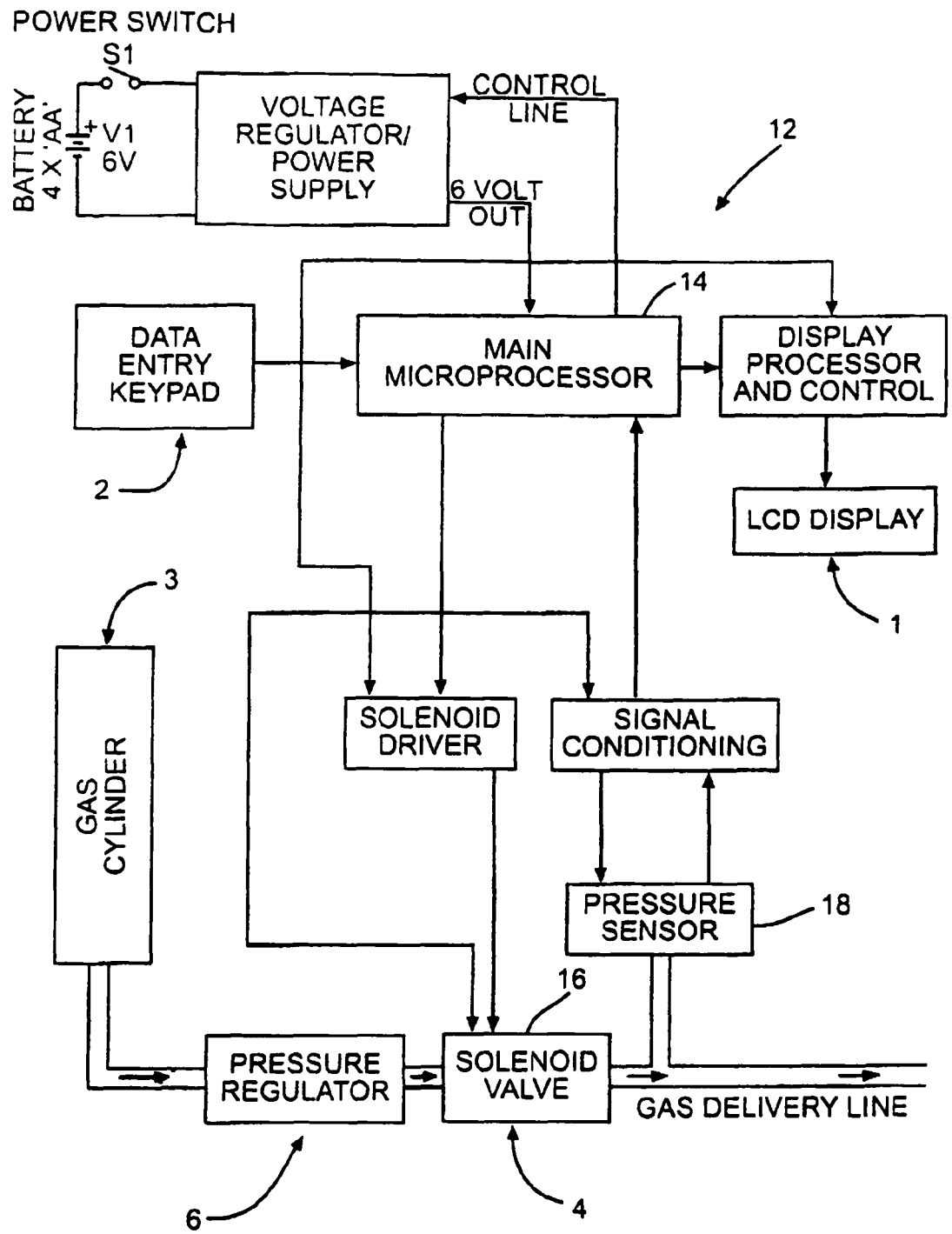
FIG. 1 illustrates an electromechanical gas delivery device.

Before the present compositions and methods are described, it is to be understood that this invention is not limited to the particular devices, compositions, methodologies or protocols described, as these may vary. It is also to be understood that the terminology used in the description is for the purpose of describing the particular versions or embodiments only, and is not intended to limit the scope of the present invention which will be limited only by the appended claims.

For simplicity, all references mentioned herein shall be deemed incorporated by reference in their entirety.

Although any methods, devices, and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

As used herein, terms such as "subject," "patient," and "mammal" may be used interchangeable. As used herein, a mammal's "airway" or "airways" refer to any of the various parts of the respiratory tract through which air passes during breathing, including, but not limited to the lungs and the trachea. As used herein, "treating excess mucus accumulation" encompasses one or more of the following: reducing mucus accumulation, preventing excess mucus accumulation, mitigating and/or preventing mucociliary dyskinesia, increasing mucociliary transport in the airway and airway inflammation. As used herein, "therapeutically effective amount" refers to an amount sufficient: (1) to increase mucociliary transport in the mammal's airway by about at least 50%; (2) to increase MMC in the mammal by at least about 50%; and/or (3) to reduce the presence of mucus in the mammal's airways by about at least 20%.

Using an equine model, the Applicants have demonstrated that the administration of gaseous NO to mammals exhibiting excess mucus accumulation is effective in the treatment thereof. Specifically, nitric oxide containing gas was inhaled by six (6) equine exhibiting excessive mucus accumulation, and immediately, within 10-30 minutes, non-viscous liquids starts to flow out of the horses' nares, resulting in reductions of mucus to trace levels in all subjects. While gaseous nitric oxide has been utilized in other therapeutic applications such as to treat pulmonary vasocontrictions, pulmonary infections, it is believed that effectiveness of gaseous NO as a mucolytic agent in treating excess mucus accumulation is novel and unexpected.

Delivering exogenous nitric oxide gas is an ideal mucolytic therapy because gaseous NO diffuses readily and uniformly into the respiratory airway to reach the mucus. Once absorbed, its biological activity is limited by avid binding to hemoglobin, rendering its activity short lived. Nevertheless, the short duration of its activity is preferred because it limits the untoward side effects of other systemic agents or drugs.

In a preferred embodiment, the administration of gaseous nitric oxide is performed using a gated flow system, and the concentration of gNO is dilutionally derived based on the mammal's inspiratory phase of the respiratory cycle. To achieve an inspiratory nitric oxide concentration of 160-220 ppm, for example, the mammal may need to receive a pre-determined higher concentration of nitric oxide and therefore a derived fraction of the mammal's tidal volume. The tidal volume of the mammal may be measured and determined using techniques well known in the art. The required flow/concentration (e.g. 160 or 220 ppm of nitric oxide) may then be calculated based on the mammal's tidal volume.

For example, a sample calculation for a horse having a tidal volume (Vt) of 7 liters per breath is as follows. Target NO dose concentration is 200 ppm. Source tank NO concentration is 10,000 ppm. Therefore, 0.02×700 (100 brs×Vt 7 liters) =14 ltrs. Duration of NO gas at Equine respiratory rate (rr) of 12/min.=8.3 mins. Total inspiratory time @ I:E ratio of 1:2=2.76 mins. Therefore NO gas flow needed @ rr of 12/min=14 ltrs./2.76=5.07 ltrs/min.

In another embodiment of the invention, the patient can be treated by administration of a therapeutically effective amount of an NO-releasing, NO-donor, or NO-upregulator compound. For simplicity, NO-releasing, NO-donor and NO-upregulators will be referred to only as "NO-releasing compounds." Known NO-releasing compounds useful in the methods and devices of the invention include, but are not limited to: nitroso or nitrosyl compounds characterized by an —NO moiety that is spontaneously released or otherwise transferred from the compound under physiological conditions (e.g. S-nitroso-N-acetylpenicillamine, S-nitroso-L-cysteine, nitrosoguanidine, S-nitrosothiol, and others described in WO 92/17445 and U.S. Pat. No. 5,427,797 (herein incorporated by reference)). In addition, other NO-releasing compounds include compounds in which NO is a ligand on a transition metal complex, and as such is readily released or transferred from the compound under physiological conditions (e.g. nitroprusside, NO-ferredoxin, NO-heme complex) and nitrogen-containing compounds which are metabolized by enzymes endogenous to the respiratory and/or vascular system to produce the NO radical (e.g. arginine, glyceryl trinitrate, isoamyl nitrite, inorganic nitrite, azide and hydroxylamine). More NO-releasing compounds are polyethyleneimine (PEI)-based polymers exposed to NO gas; molsidomine; nitrate esters; sodium nitrite; iso-sorbide didinitrate; penta erythritol tetranitrate; nitroimidazoles; complexes of nitric oxide and polyamines; anionic diazeniumdiolates (NONOnates) (including those disclosed in U.S. Pat. Nos. 4,954,526 and 5,155,137) and the NO releasing compounds disclosed in U.S. Pat. No. 5,840,759 and PCT WO 95/09612. Examples of NONOate compounds include diethylamine/NONO, diethylenetriamine/NONO, and methylaminohexylmethylamine/NONO (illustrated in Hanson et al., Nitric Oxide, Biochemistry, Molecular Biology, and Therapeutic Implications, Ignarro and Murad, Ed., Academic Press, New York (1995)). An NO-releasing compound, donor or upregulator can be provided in powder form or as a liquid (e.g., by mixing the compound with a biologically-compatible excipient).

The NO-releasing compound can be administered to the patient alone or in conjunction with NO gas, CO gas, a carrier gas or another NO-releasing compound. When more than one compound is administered to the patient, the compounds can be mixed together, or they can be administered to the patient sequentially. Any one, or a combination, of the following routes of administration can be used to administer the NO-releasing compound(s) to the patient: intravenous injection, intraarterial injection, transcutaneous delivery, oral delivery, and inhalation (e.g., of a gas, powder or liquid).

The NO-releasing compound selected for use in the method of the invention may be administered as a powder (i.e., a finely divided solid, either provided pure or as a mixture with a biologically-compatible carrier powder, or with one or more additional therapeutic compounds) or as a liquid (i.e., dissolved or suspended in a biologically-compatible liquid carrier, optionally mixed with one or more additional therapeutic compounds), and can conveniently be inhaled in aerosolized form (preferably including particles or droplets having a diameter of less than 10 μm). Carrier liquids and powders that are suitable for inhalation are commonly used in traditional asthma inhalation therapeutics, and thus are well known to those who develop such therapeutics. The optimal dosage range can be determined by routine procedures by a pharmacologist of ordinary skill in the art. For example, a useful dosage level for SNAP would be from 1 to 500 μmoles (preferably 1-200 μmoles) per inhaled dose, with the number of inhalations necessary varying with the needs of the patient.

When an NO-releasing compound is inhaled in solid or liquid form, the particles or droplets are deposited throughout the respiratory system, with larger particles or droplets tending to be deposited near the point of entry (i.e., in the mouth or nose) and smaller particles or droplets being carried progressively further into the respiratory system before being deposited in the trachea, bronchi, and finally the alveoli. (See, e.g., Hounam & Morgan, "Particle Deposition", Ch. 5 in Respiratory Defense Mechanisms, Part 1, Marcel Dekker, Inc., NY; ed. Brain et al., 1977; p. 125.) A particle/droplet diameter of 10 .mu.m or less is recommended for use in the method of the invention. Determination of the preferred carrier (if any), propellant (which may include NO diluted in an inert gas such as $N_2$), design of the inhaler, and formulation of the NO-releasing compound in its carrier are well within the abilities of those of ordinary skill in the art of devising routine asthma inhalation therapies. The portable inhaler could contain an NO-releasing compound either mixed in dry form with a propellant or held in a chamber separate from the propellant, or mixed with a liquid carrier capable of being nebulized to an appropriate droplet size, or in any other configuration known to those skilled in portable inhaler technology. A few of the several types of inhaler designs that have been developed to date are discussed in, for example, U.S. Pat. Nos. 4,667,668; 4,592,348; 4,534,343; and 4,852,561, each of which patents is herein incorporated by reference. Other inhaler designs are described in the Physicians' Desk Reference, 45th Edition, Edward R. Barnhart, Publisher (1991). Each of these and other aerosol-type inhalers can be adapted to accommodate the delivery of NO-releasing compounds. Also useful for delivering an NO-releasing compound formulated in dry powder form is a non-aerosol-type inhaler device such as that developed by Allen & Hanburys, Research Triangle Park, N.C.

The following examples describes the manner and process of administration of gaseous nitric oxide to equines that reduces excess mucus accumulation and increases mucociliary clearance according to the present invention. The following example should not be construed as limiting.

Example 1

Six (6) Thoroughbred racehorses at a major racing jurisdiction were quarantined for two weeks, and each horse had evidence of excessive mucus production as surveyed by clinical presentation and by endoscopic exam. The horses were isolated from each other and were being medicated daily in series with several broad-spectrum antimicrobials routinely employed for respiratory infections in Equids. The results before the administration with gaseous NO had been unremarkable. Further physical exam revealed all other systems were within normal limits. All six horses were included in the study using gaseous NO.

Intervention/Methods:

The horses were brought individually to the veterinary hospital barn for further evaluation over the course of five days. An fiberoptic endoscope was passed to the level of the bifurcation of the trachea (carina-airway) with images recorded on videotape. A scoring system was used to indicate the presence or absence of mucus, as well as its severity, if present. This scoring system has been described by Dixon et.

al., "Equine Pulmonary Disease: Ancillary Diagnostic Findings," Equine Vet. Journal 27, 428-435, 1995, herein incorporated by reference in its entirety. A score of zero indicates the absence of mucus, while a score of 1 to 5 indicates increasing amounts of mucus observed endoscopically in the trachea. The attending Veterinarian conducting the examination did the scoring. All of the six horses scored 4 or higher before the initiation of the treatments.

Treatment intervention of inhaled gaseous Nitric Oxide was administered to all six horses during a five-day period. Five of the horses (#2-#6) received 100 breaths of 10,000 ppm resulting in, based on pulmonary mechanics, a lung concentration of approximately 160 ppm. Horse #1 received 100 breaths of 5000 ppm resulting in 80 ppm on Day #1 and a second administration of 100 breaths of 10,000 ppm on Day #5. Horse #5 received 100 breaths of 10,000 ppm on Day #3 and a second administration of 100 breaths of 10,000 ppm on Day #4.

It was observed that immediately following the administration of gaseous NO to the horses that non-viscous liquids started to flow out of the nares of the horses. The liquids appear to be mucus that has been hydrolyzed and thinned, and Applicants postulate that gaseous NO hydrolyzes the mucus by breaking down disulfide bonds and/or affecting cysteine moieties in the mucus gel matrix.

The method of the inhaled NO administration was uneventful to other physiological systems and no untoward side effects were observed. An outline of the treatment results is provided below in Table No. I (with scores when available). At Day #1, all subjects had a score of 4 or greater. On a day where a measurement and a treatment occur, such as Day #4 for Horse #5, the measurement was taken before the administration of the second dosage.

TABLE NO. 1

|  | Day #1 | Day #2 | Day #3 | Day #4 | Day #5 | Day #6 |
|---|---|---|---|---|---|---|
| Horse #1 | Tx, 5k | Clear (0) | 25% rtn. | NG | NG, Tx 10k | Trace (1) |
| Horse #2 | Tx, 10k | Clear (0) | 25% rtn. | NG | NG | NA |
| Horse #3 | NA | Tx, 10k | Clear (0) | NG | Trace (2) | NA |
| Horse #4 | NA | NA | Tx, 10k | Clear (0) | 25% rtn. | NA |
| Horse #5 | NA | NA | Tx, 10k | Clear (0), Tx, 10k | Trace (2) | Trace (1) |
| Horse #6 | NA | NA | NA | NA | Tx, 10k | Trace (2) |

Legend:
NA = Not applicable, not available for review
NG = No change in status
25% rtn = A return of 25% of the previous amount of mucus (amount before administration of gNO), not scored
Tx, 5k = A treatment using 100 breaths at 5000 ppm
Tx, 10k = A treatment using 100 breaths at 10,000 ppm
(0-2) = Numerical scoring system Although, not scored for the horses in which 25% of the mucus returned (Horses #2 and #4), a 75% reduction in mucus from Day #1 was observed in these horses. In Horses #1, #3, #5 and #6, a reduction in mucus scores of 4 and 5 to trace amounts (score 1 and 2) demonstrates a reduction of about 40% to about 80% of mucus present in the airways.

Preliminary experiments with bovine show similar effectiveness with mucus being hydrolyzed and excreted from the nares within 10-30 minutes. Anecdotal studies with human volunteers with the flu show similar effectiveness. Thus, the Applicants believe that inhaled gaseous NO as an effective treatment to excess mucus accumulation in the airways of mammals.

It is believed that the observed reduction in the presence of mucus was through the immediate mucolytic activity of gNO in breaking down the mucus gel matrix. While the NO molecule has been studied for many purposes, it is believed that the use of inhaled gaseous NO as a suitable mucolytic therapy is novel. Once liquefied, the ciliary appendages in the respiratory epithelial cells may then more easily transport and move the mucus to clear the respiratory airway.

Similarly, it is believed NO contributes to the motility of the airway epithelium thereby assisting in the regulation of mucociliary transport in the respiratory tract. (Nikon Kokyuki Zasshi, 2000 August, 38 (8):585-8) and (Tamaoki J et al, J Aerosol Med. 2000 Fall; 13(3):239-44). Other investigators (Imada M et al (Acta Otolaryngol. 2002 July; 122(5): 513-9) likewise demonstrated a shortened transport time and increased mucociliary clearance using topical nitric oxide donors (e.g., SNP). Inhaled Nitric Oxide (INO) gas acts as an anti-inflammatory agent by decreasing neutrophil numbers and their major chemoattractant, IL-8. INO may also increase cell apoptosis in the lungs during inflammatory conditions, which may explain, in part, how it resolves pulmonary inflammation.

It is also believed that Nitric Oxide may be influencing the substrate glutathione and its precursor acetylcysteine to cleave disulfide bonds facilitating the removal of organized mucus and bronchial secretions (Ramnarine S I et al, British Journal of Pharmacology. 118(4): 998-1002, 1996 June) (Professor Valerie m. Hudson, David M. Kennedy Center for International and Area Studies, 212 HRCB, Brigham Young University, Provo, Utah 84602, USA).

Moreover, delivery of gaseous NO may increase the local bioavailability of nitric oxide that may regulate and increase the ciliary beat frequency of the respiratory epithelial cells. This leads to further ameliorating of mucociliary dyskinesis with subsequent decreased mucociliary transit time Further, because of the anti-infective activity of gaseous NO, longer duration and treatment profiles may be beneficial in removing the microbes or virus that may be causing the excess mucus secretion and accumulation.

Determining the treatment eligibility of an individual may be based upon the clinical presentation of excessive mucus accumulation in the upper lower airway. The excessive mucus accumulation may be observed with an endoscope. A therapeutic amount of nitric oxide containing gas may be administered to a mammal to reduce the amount of mucus in the airways by at least about 20%, preferably at least about 50%, and more preferably, at least about 75%. The scoring system described by Dixon et al. 1995 provides a qualitative measure of the presence or absence of mucus, using a scale of 0-5. Thus, a therapeutic amount of nitric oxide containing gas inhaled by a subject may be effective in decreasing this mucus score by at least 1 point, or by about 20%. Other means of quantifying mucus in the airways are also possible.

Additionally, inhaled nitric oxide containing gas may act as a preventative measure in the accumulation of mucus in the airways. Mammals may be selected that exhibit a risk of mucus accumulation. Such a risk may be associated with recent infection and/or contact with other infected mammals. Preliminary experiments with healthy bovine show that delivery of inhaled gNO results in the prevention of mucus accumulation. Additionally, in the equine study, the delivery of gNO did not result in any irritation, inflammation or abnormal side effects. The delivery of inhaled nitric oxide containing gas may be administered to these risk mammals in order to prevent mucus accumulation in the airway. Effective therapeutic amounts may also refer to an amount sufficient to break down the viscoelastic mucus and increase mucociliary transport in the mammal's airway and to increase MMC in the mammal. Therefore, treating mucus accumulation in the airways of a mammal comprises reducing mucus accumulation, preventing mucus accumulation, reducing mucociliary dyskinesia, and/or preventing mucociliary dyskinesia.

Example 2

Twenty-seven Standardbred horses were referred to this study with a history of poor performance and with evidence of excessive mucus accumulation as surveyed by endoscopic exam. This was a single site population study and the subjects served as their own control.

Intervention/Methods:

All twenty-seven horses were given inhalant Nitric Oxide gas in the most effective concentrations as determined from previous empirically derived observations. Horses were examined pretreatment by videoendocscopy on a minimum of two consecutive occasions post race, one week or longer between scopings, to document the degree and persistence of mucus residence. The endoscope was passed to the level of the bifurcation of the trachea (carina) with images logged on a video recorder. The Dixon et al. scoring system was used to indicate the presence or absence of mucus, as well as its severity, if present. Zero indicates absence of mucus, and 1 to 5 indicating increasing amounts of mucus observed endoscopically in the trachea. Scoring was done by the veterinarian conducting the examination, then later by another "blinded" individual using the recorded examination.

Treatment via a metered delivery device was provided that included a source of nitric oxide from a pressurized gas cylinder and a delivery interface with the subject's nare. The Nitric Oxide delivery device is enabled by a microprocessor-based computer (Pulmonox Medical Inc, Tofield, Alberta, Canada) wherein a proportionate flow rate of Nitric Oxide gas is delivered based on the horse's tidal volume/minute ventilation with a resulting airway/pulmonary concentration of 160-200 ppm.

Upon enrollment in the study a candidate for the treatment intervention was administered 100 breathes of NO gas as previously described for a minimum of three days. A follow up endoscopic exam on the next available immediate post race was performed and a mucus score assigned. Post race endoscopic exams were continued for several events as a measurable outcome. Depending on the results (i.e. no change or a graded increase in mucus scores) multiple treatment cycles were continued and the results recorded via post race endoscopic exam over the next of several weeks.

TABLE 2

| Horse | Pre-Mucus Score | Post-Mucus Score (after administering gNO) | Decrease in Mucus Score |
|---|---|---|---|
| 1 | 3.5 | 0 | 3.5 |
| 2 | 2 | 0 | 2 |
| 3 | 3 | 1 | 2 |
| 4 | 2 | 1 | 1 |
| 5 | 3 | 1 | 2 |
| 6 | 2.5 | 2 | .5 |
| 7 | 3 | 2 | 1 |
| 8 | 3 | 2 | 1 |
| 9 | 2.5 | 0 | 2.5 |
| 10 | 3.5 | 3 | .5 |
| 11 | 3 | 0 | 3 |
| 12 | 3 | 4 | X |
| 13 | 3 | 0 | 3 |
| 14 | 3.5 | 0 | 3.5 |
| 15 | 2 | 1 | 1 |
| 16 | 4.5 | 1.5 | 3 |
| 17 | 2.5 | 2 | .5 |

TABLE 2-continued

| Horse | Pre-Mucus Score | Post-Mucus Score (after administering gNO) | Decrease in Mucus Score |
|---|---|---|---|
| 18 | 2.5 | 2 | .5 |
| 19 | 4 | 1.5 | 2.5 |
| 20 | 2 | 0 | 2 |
| 21 | 3.5 | 2.5 | 1 |
| 22 | 2.5 | 2 | .5 |
| 23 | 4 | 2.5 | 1.5 |
| 24 | 5 | 3 | 2 |
| 25 | 4.5 | 4 | .5 |
| 26 | 3 | 2.5 | .5 |
| 27 | 2.5 | 2.5 | 0 |

Of the twenty-seven horses enrolled in the study all but two showed significant improvement in their mucus scores (a decrease in scores from control) post treatment. Twenty five horses experienced a decrease in score by at least 0.5 on the Dixon et al. scale. Eighteen horses demonstrated a marked reduction in endoscopy scores on post treatment endoscopic exam after a single treatment cycle with a score reduction of at least 1. Twelve subjects experienced a significant but transient reduction in endoscopy scores with either a single or multiple treatments, decreasing in mucus score from 2 to 3.5. Two subjects had a muted response to one or more treatments. One subject was discounted due to biased post race Exercise Induced Pulmonary Hemorrhage on multiple exams. Due to the realities of the racetrack environment there was a considerable amount of time variability in both the initiation of the treatment cycle after enrollment in the study and on follow up post race exams. In addition those horses that demonstrated a recurrence to 2 or > scores in the weeks following the first treatment received additional treatment cycles with a repeatable marked reduction in mucus scores following treatment.

Examples of Delivery Methods and Devices

Various methods and devices may be used to administer a therapeutically effective amount of nitric oxide containing gas to a mammal's airways. While preferred examples are provided herein, they are not intended to be limiting.

Effective therapeutics may include an administration of nitric oxide containing gas in a defined concentration of parts per million for a finite duration. Preferably, the target concentration of nitric oxide mammal's airways ranges from about 80 ppm to 400 ppm, and more preferably from about 160 ppm to about 220 ppm.

Delivery of nitric oxide gas to the airway may be achieved through delivery that coincides with the inhalation of the subject. In one embodiment for use with humans, gNO may be contained within portable pressurized canisters such as those used with portable inhalers that are well known in the art. Examples of inhaler designs are discussed in, for example, U.S. Pat. Nos. 5,823,180; 5,570,683; 4,667,668; 4,592,348; 4,534,343; and 4,852,561, each of which patents is herein incorporated by reference. Other inhaler designs are described in the Physicians' Desk Reference, 45th Edition, Edward R. Barnhart, Publisher (1991). Each of these and other aerosol-type inhalers can be adapted to accommodate the delivery of NO gas. This embodiment is especially suited for use by individuals suffering from, for example, common colds or allergy, congestive cough, and flu.

In use, the pressurized canister includes a release valve that can be manually actuated to controllably release gNO into a channel or tube adapted for insertion into the mouth or nostril of the mammal. Coincident with, or immediately before the inhalation by the mammal, the release valve can be actuated so as to release the gNO into the oral or nasal cavity and inhaled into the respiratory airway. Successive treatments and release of gNO coincident with the inspiration can be made depending on the therapeutic dosage. The amount of gNO release preferably ranges from about 0.5 ml to about 8 ml at a canister concentration of about 5000 or 10,000 ppm.

A visible label can also be affixed to the pressurized canister indicating that gNO is used as a mucolytic agent to treat excess mucus accumulation or as an expectorant. Additionally, the pressurized canister can be included in a kit that also includes instruction for its use to treat excess mucus accumulation in the airway. Preferably, the instruction instructs the user that exhibits excess mucus accumulation to insert the channel into his mouth or nostril and to actuate the release valve substantially coincident with the inhalation by the user.

In another embodiment envisioned for use in a hospital or clinical setting, breathable air from any source (e.g., ambient room air or ventilator carrying oxygen containing gas) may be directed to a nasal interface using techniques well known in the art. The inspiration and expiration flow rates of a spontaneous breathing of a mammal may be monitored using a flow sensor or flow meter known in the art and, inspiration flow profiles can be determined for the mammal's breathing. Inspiration flow profile of the breathable gas is the flow rate of the gas as a function of inspiration time. Delivery of the NO containing gas, preferably added to the breathable gas stream through a Y-piece connector, may be timed to coincide with the mammal's inspiration.

In the embodiments described to deliver the nitric oxide containing gas coincident with inspiration, the concentration of the gas delivered is dilutionally derived and is based on the individual's tidal volume. Thus, the final concentration of nitric oxide gas at the treatment site is a function of arbitrary flow rates and starting concentration. Accordingly, starting concentrations of gNO that are higher than the desired concentration for therapeutic effectiveness may be needed to account for the dilution by the breathable air flowing into the airway, and flow rates may be regulated flow rates may be regulated For example, in humans, if the desired therapeutic concentrations of nitric oxide in the nitric oxide containing gas is about 160 ppm to about 220 ppm in the lungs, then the source gas may need to contain concentrations of nitric oxide of about 5000 ppm to about 10,000 ppm. In order to meet the therapeutic level in certain embodiments, a delivery concentration of the nitric oxide may need to be decreased by about 80-90 percent to account for dilution with breathable gas in a human patient. These values of nitric oxide containing gas may be delivered to a patient during their inspiration, wherein for example, a human patient is breathing at a flow rate of about 1 liter per minute. Under this example, delivered nitric oxide containing gas having a concentration of about 5000 ppm at 1 liter per minute would be reduced to a concentration of about 65 ppm in the lungs when diluted by the breathable air. If the flow rate is changed to 2 liter per minute, then the delivered nitric oxide containing gas should have a concentration of about 5000 ppm to maintain the same concentration of about 130 ppm at the treatment site (therapeutic concentration). As another example, a pulse of about 1 to 1.5 seconds of nitric oxide would deliver 100 to 150 milliliters of nitric oxide into the airway and the lungs.

These calculations in humans may be recalculated using any concentration of source gas, using the tidal volume of human, which is about 0.5 mL per breath. If a source gas of 10,000 ppm is used and a target therapeutic concentration is 200 ppm, knowing that the tidal volume is 0.5 mL/bth, 1 liter of the gNO may be delivered over 100 breaths. A typical respiratory rate of a human is 12 bth/min, resulting in a treatment time of about 8.33 minutes. As another example, if a source gas of 10,000 ppm is used and a target therapeutic concentration is 100 ppm, about 0.5 liter of the gNO may be delivered over about 100 breaths. Calculations may be based on total minute ventilation of a patient, which is respiratory rate multiplied by tidal volume, for example is 0.5 L/bth×12 bth/min=6 L/min. An inspiratory ratio of 1:2 may be used with a human patient, resulting in a inspiratory time ratio of 0.33. A total inspiratory time per treatment may then be calculated multiplying the inspiratory time ratio by the treatment time, or 8.33 min×0.33=2.78 min, in this example. An inspiratory gNO flow rate from device may be calculated by dividing the source gNO required per treatment by the total inspiratory time, or 0.5 L/2.78 min=0.18 L/min.

In the equine model, flow rates of nitric oxide containing gas will be greater than in the human model to account for greater tidal volume of the horse (about 7 liter per breath). However, horses take about the same number of breaths per minute as humans, about 12 per minute at rest. The flow values outlined below in Table No. 3 provide a guide that allows for effective delivery of near optimal concentrations of the gas using a source cylinder concentration of 10,000 ppm of gaseous NO.

TABLE NO. 3

| Subject tidal volume Flow (7-8 ltrs) | Target Nitric Oxide Delivery (ppm) | NO Inspiratory Flow from device (100 brs.) |
| --- | --- | --- |
| At rest | 160 | 4.0 ltrs/min |
| At rest | 200 | 5.07 ltrs/min |

As alluded to above, the nitric oxide containing gas may be inhaled over a finite period of consecutive breaths. In equine, nitric oxide containing gas may be combined and delivered to about 100 consecutive nasal breaths. For example, using a 10,000 ppm nitric oxide gas source delivered coincident with the inspiratory flow of the horse in 100 breaths results in, based on pulmonary mechanics, a lung concentration of approximately 160 ppm. Using 5,000 ppm nitric oxide gas source in 100 breaths results in about 80 ppm.

With a source gas of 5000 ppm and a target therapeutic delivery concentration of 200 ppm, 28 liters of NO gas should be delivered over 100 breaths. The deliver treatments would be delivered over 8.33 minutes. Total minute ventilation for a horse would be tidal volume (7 L/bth) multiplied by respiratory rate (12 bth/min), or 84 L/min. An inspiratory ratio of 1:2 may be used with a horse, resulting in an inspiratory time ratio of 0.33. A total inspiratory time per treatment may then be calculated multiplying the inspiratory time ratio by the treatment time, or 8.33 min×0.33=2.78 min, in this example. An inspiratory gNO flow rate from device may be calculated by dividing the source gNO required per treatment by the total inspiratory time, or 28 L/2.78 min=10.08 L/min.

In yet another embodiment, triggering of the NO flow into the breathable gas stream may also be accomplished by measuring and modeling the mammal's inspiration profile for a number of previous breaths. NO flow is then initiated on a subsequent breath based upon a predicted timing of the mammal's breathing to flow NO during inspiration. Yet another alternative method of determining the point to initiate the NO flow is by measuring the volume inspired by the mammal, which can be calculated based on the flow rate and elapsed time of flow of the breathable gas.

Those in the respiratory art, and particularly those familiar with ventilation methods, recognize the respiratory cycle of the mammal. The respiratory cycle is synchronous, defined by the inhalation and exhalation of the mammal. There are several synchronous parameters that may be observed to determine the inhalation and exhalation phases of the cycle. Examples of these parameters include the rate of flow of gas directed toward the mammal's airway, pressure change at the initiation of a breath, the synchronous movement of the laryngeal, and the synchronous motion of the chest wall. One or more of these parameters may be used as an indicator of the timing of mammal inhalation and exhalation. Thus, a synchronous parameter may be used to determine the initiation of a breath, and delivery of gNO may be timed according to the synchronous parameter to coincide with the inspiration of the mammal. This parameter may not be applicable to all mammals as anatomy will vary.

The above methods are preferably performed through the use of a control module, preferably a controller such as a computer microprocessor with associated logic (firmware or software), that may time the administering of the nitric oxide containing gas to the mammal's airway. The timing may be during the mammal's inspiration, at a predetermined or pre-measured time. Alternatively, the mammal's inspiratory flow or volume may be measured and thus delivery will coincide with this measurement. This volume may be monitored or adjusted based on successive breaths.

In another embodiment, a pulse dose delivery or a bolus injection delivery of the NO containing gas may be used. The timing of the bolus injection may be correlated to the detection or observation of a mammal breath. For example, a bolus injection of the NO containing gas may be delivered nasally or orally substantially coincident with the inhalation.

Systems and apparatus for delivery of nitric oxide containing gas have been described, for example, in U.S. patent application Ser. No. 10/315,539 (Publication No. 2003/0150457), which is herein incorporated by reference in its entirety. In that application, a nitric gas dispenser is described, which gates the flow rate of the gNO to the inspiratory phase of the respiratory cycle. The dispenser may also include a pressure sensor and a valve mechanism for controllably delivering the nitric oxide gas in connection with the subject's breathing. Synchronous inspiratory application may be advantageous and necessary in order to quantify inhalant nitric oxide administration and minimize inadvertent human and/or mechanical error.

With reference to the FIGs., which describe a delivery method to a horse, FIG. 1 illustrates a block diagram representation of the device 12. With reference to FIG. 1, the device 12 has a power source 100. The power source can be an electrical outlet if the user of the device is going to work out on a treadmill or a battery if the user will be working away from a confined environment like a track. The power source 100 provides sufficient voltage and charge to properly operate the device 12. The device 12 also has a controller that comprises main microprocessor 14 that controls the operation of a solenoid valve 16, also within the device 12. The solenoid valve 16 operates in conjunction with operating parameters that are entered via a data entry keypad 2 and the input from a pressure sensor 18.

The operating parameters and the operating status of the device 12 are displayed on an LCD display 1. Along with the LCD display 1, the device 12 has a nitric oxide gas supply 3, preferably a cylinder. In that cylinder is nitric oxide having a pressure of 1800 to 2200 or even as low as 500 pounds per square inch (psi).

The device 12 also has a pressure regulator 6. The pressure regulator 6 reduces the pressure of the nitric oxide to less than 100 psi so it can be administered to the mammal, such as a horse, without damaging the mammal's organs from too much pressure.

Calibrating the flow through the solenoid valve 16 is obtained by selecting the pressure of the pressure regulator 6 and controlling the time that the solenoid valve 16 is open. Thereby, the valve 16 allows a precise amount of nitric oxide to be delivered through a gas delivery line 4, which delivers the nitric oxide to the mammal, preferably a horse. The pressure sensor 18 is designed to detect a drop in pressure in the gas delivery line 4, when the horse initiates a breath. This pressure drop signals the main processor 14 to open the solenoid valve 6 for a pre-programmed period of time. Among the parameters that are programmed into the device are: Total Breaths, Start Delay, Pulse Time, Pulse Delay, and Re-trigger Lock.

The programmable parameters are defined as follows:

Total Breaths: This parameter is the number of breaths programmed into a run. Each time a breath is detected as identified above, a pulse of nitric oxide gas is injected into the breath of mammal. Breaths that occur during a locked out time of the run are not counted as breaths. After the programmed number of breaths are counted, the run stops automatically and nitric oxide gas is no longer injected into any breaths of the mammal. This number can be set anywhere from 0 to 100 breaths. If the number is set at 0 then the auto shutoff is disabled and breaths will be injected with nitric oxide until the user stops the run.

Start Delay: This parameter is the programmed delay time in minutes that the user can set. The injection of nitric oxide gas into each breath will begin automatically after "Start Delay" minutes. It will then continue for the number of Total Breaths and then the device 12 stops automatically.

Pulse Time: This parameter is the length of time that the solenoid valve 16 will open for delivery of nitric oxide gas. The resolution is 0.1 seconds and the range is 0.1 sec to 0.9 seconds. If the regulator is set at 50 psi then each second of the solenoid valve 16 opening 31 cc of nitric oxide gas. If the regulator pressure is set at 30 psi then each 0.1 sec solenoid valve 16 opening represents 21 cc of nitric oxide gas. For example, if the regulator is set at 50 psi and the pulse time is set at 0.3 seconds then each detected breath will be injected with a pulse of 0.3 seconds or about 90 cc of nitric oxide gas.

Pulse delay: This parameter is the length of time that the machine waits after detecting the beginning of a breath before opening the solenoid valve 16 to inject a pulse of nitric oxide gas. This allows the user to control the position of the bolus of nitric oxide gas in the breath. For example, if the user sets the solenoid valve 16 at 0.4 seconds, then 0.4 seconds after the beginning of the breath is detected the solenoid valve 16 will open to inject the nitric oxide pulse.

Retrigger Lock: This parameter is the total time that the machine will ignore new breaths beginning at the detection of a new breath. If this parameter is set at 4.5 seconds then the device 12 will wait, after detecting a breath, for 4.5 seconds before recognizing a new breath. Full or half breaths that are initiated by the animal during this lockout time will not be counted and no nitric oxide will be injected. If the breath is initiated before the lockout expires and the animal is still inhaling when the lockout expires then it will be recognized as a new breath and it will be counted and injected with nitric oxide.

Figure 2:
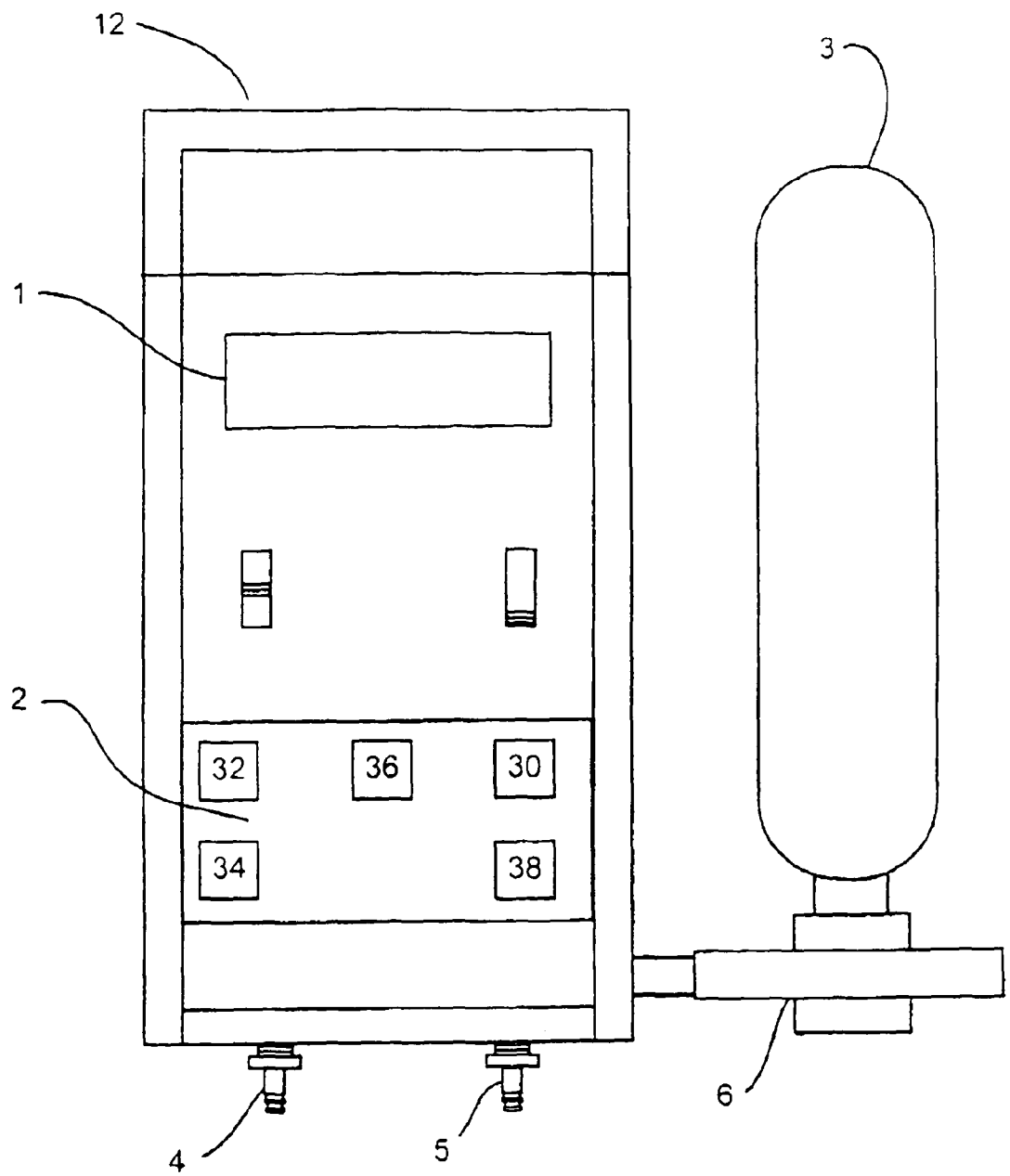
FIG. 2 represents the device described in FIG. 1.

With reference to FIG. 2, the data entry keypad 2 contains five active button switches defined as follows:

START/PULSE KEY 30: This key is used to start a run. The user is required to confirm the start by pressing an UP key 32 or to cancel by pressing a DOWN key 34. When a run is in progress, pressing this key will cause the run to pause. The run is then resumed by pressing the UP key 32 or stopping the run by pressing the DOWN key 34.

UP key 32: This key is used to confirm the start of the run, to resume a paused run and also to increment valve changes.

DOWN key 34: This key is used to cancel a started run, end a paused run and also to decrement valve changes.

NEXT key 36: This key is used to switch screen pages on the LCD display 1.

PURGE key 38: This key is used to open the solenoid valve 16 for two seconds to purge the line. This key is not active during a run. The LCD display 1 displays four screen pages, defined as follows:

Each screen page displays a status line. The status variations include NOT RUNNING, WAITING, RUNNING, PAUSED, PURGING and START Pressed.

The main screen page has a row of asterisks on the top line. This is the only screen available when the KEY switch is in the locked position. This screen displays the total breaths detected and also the total breaths that will cause the run to stop.

The second page shows two valves. The first is the START DELAY valve. When the screen first appears the blinking cursor shows the value, which can be changed by pressing either the UP or DOWN key. Pressing the NEXT key switches, the cursor to the second value on the screen which is TOTAL BREATHS.

The third page allows the user to change the PULSE DELAY and the PULSE TIME.

The fourth page allows the user to change the RETRIGGER LOCK.

With reference to FIG. 2, a capped port 5 is depicted. This is an alternate input port fir nitric oxide and is utilized if the device is not used with the small gas cylinder as depicted in FIG. 2. The cap is typically replaced with a quick-connect style fitting for attachment to a standard regulators on a large gas cylinder.

In one embodiment, the controller may also comprise logic such as firmware or software for selection of a therapeutic profile for the administration of gaseous nitric oxide based on an input value representing a level of severity of mucus accumulation in the mammal's airway. The level of severity may be determined by an attending physician or veterinarian using, for example, a fiberoptic endoscope, as described in the study with horses. As an example, the input value may be 0, 1, 2, 3, 4, and 5, wherein 5 indicates a most severe condition of excess mucus accumulation, while 0 represents only a trace amount of mucus. It should be understand that there are many variations on the types of input value, (e.g., A, B, C, et seq. or High Medium, Low, et seq., Most Severe, Severe, Medium, Trace, None), and these variations are considered as equivalents to a numerical scale.

The controller may further comprise a memory device such as a RAM, ROM, EPROM, hard disk, removable storage medium or other removable known in the art, wherein the memory device stores a number of therapeutic profiles each corresponding to a level of severity of mucus accumulation in the mammal's airways. The therapeutic profiles can be predetermined or programmable by the user. The parameters that make up the therapeutic profiles may include, but is not limited to, flow rate of nitric oxide containing gas, duration of administration of nitric oxide containing gas, number of breaths for which nitric oxide containing gas is to be administered, and concentration of therapeutic NO delivered to the airways.

In use, an attending physician or veterinarian makes a diagnosis of the severity of excess mucus accumulation in the mammalian's airway. The attending physician or veterinarian then input a value into the device 12 or select a value from a set of presented values by the device 12 via the data entry keypad 2. The device 12 via the controller is then instructed to execute the delivery of a certain therapeutic profile corresponding to the value inputted or selected. Table 3 illustrates a sample set of therapeutic profiles based on a nitric oxide gas source at 10,000 ppm for delivery to an equine. It should be understand that this example is not intended to be limiting, and other types of therapeutic profiles may be programmed into the device and delivered to the mammal.

TABLE NO. 4

| Time Dose Profiling (10% reduction steps on No Breaths) | | | | |
|---|---|---|---|---|
| Input Value | flow rate | duration of administration | No. of breaths | Pre-Diagnosis |
| 0 | | | | |
| 1 | 4.0 ltrs./min. | 8.30 mins. | 100 (160 ppm) | Mucus Score 1 |
| 2 | 5.07 ltrs./min. | 2.07 mins. | 25 (200 ppm) | Mucus Score 2 |
| 3 | 5.07 ltrs./min. | 4.15 mins. | 50 (200 ppm) | Mucus Score 3 |
| 4 | 5.07 ltrs./min. | 6.23 mins. | 75 (200 ppm) | Mucus Score 4 |
| 5 | 5.07 ltrs./min. | 8.30 mins. | 100 (200 ppm) | Mucus Score 5 |

Figure 3:
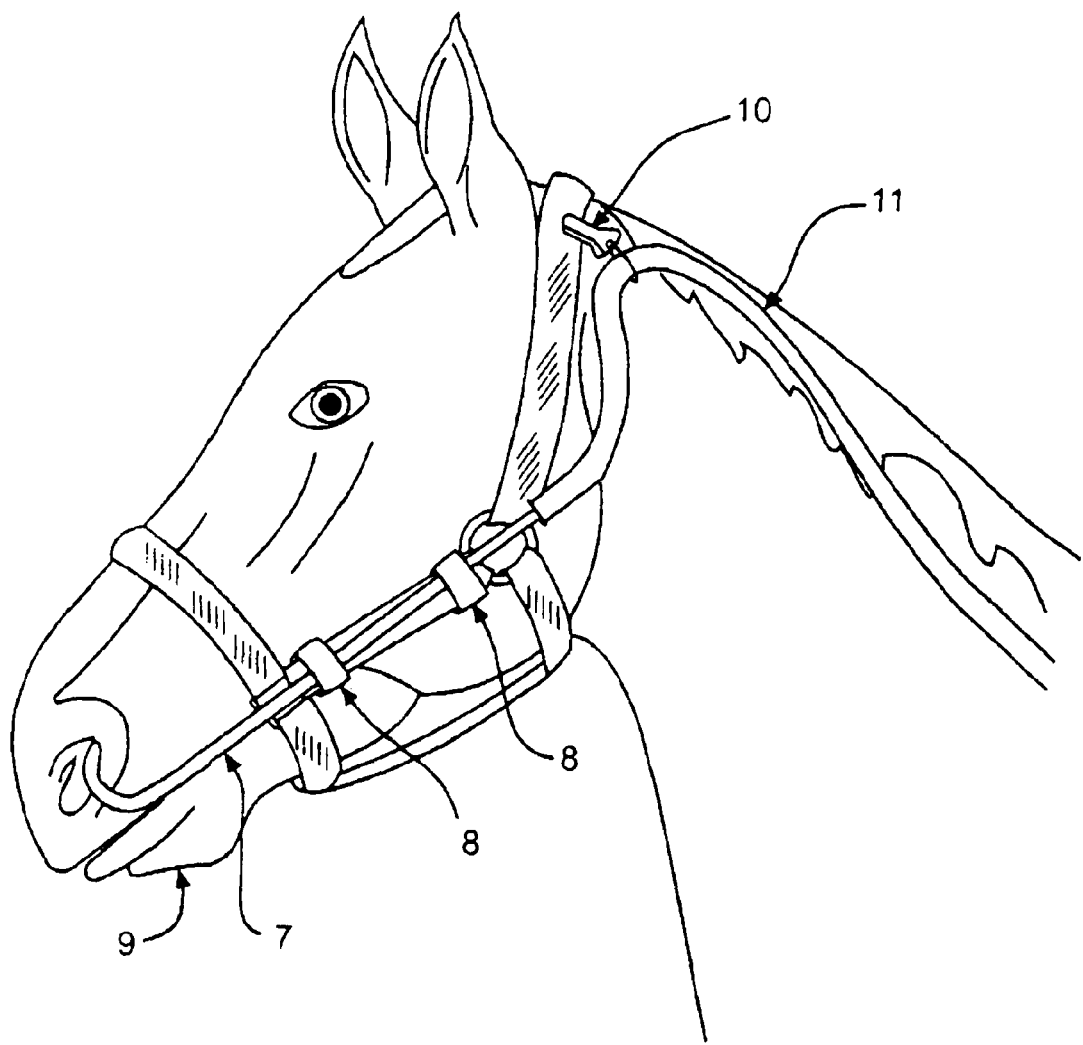
FIG. 3 illustrates a method of delivery of the gas to a horse.
Figure 5:
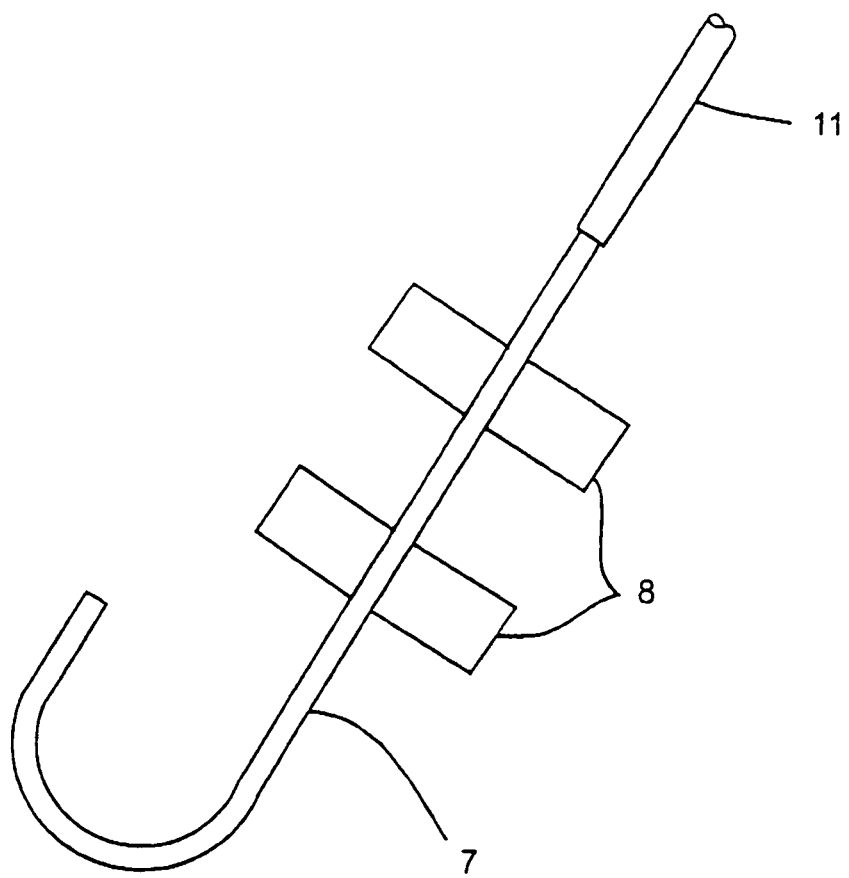
FIG. 5. illustrates a J-tube used in conjunction with the device to induce gas into the nostril of a horse.

FIGS. 3 and 5 illustrate the method of delivering nitric oxide to the horse. A J-tube 7 made of semi rigid plastic such as styrene is attached to the horses' halter 9 by two hook and loop fabric fasteners. A small clip 10 also secures the delivery line 11 to the halter 9. The delivery tube 11 is typically a clear plastic flexible tubing. The delivery line connects to port 4 shown in FIG. 2.

Figure 4:
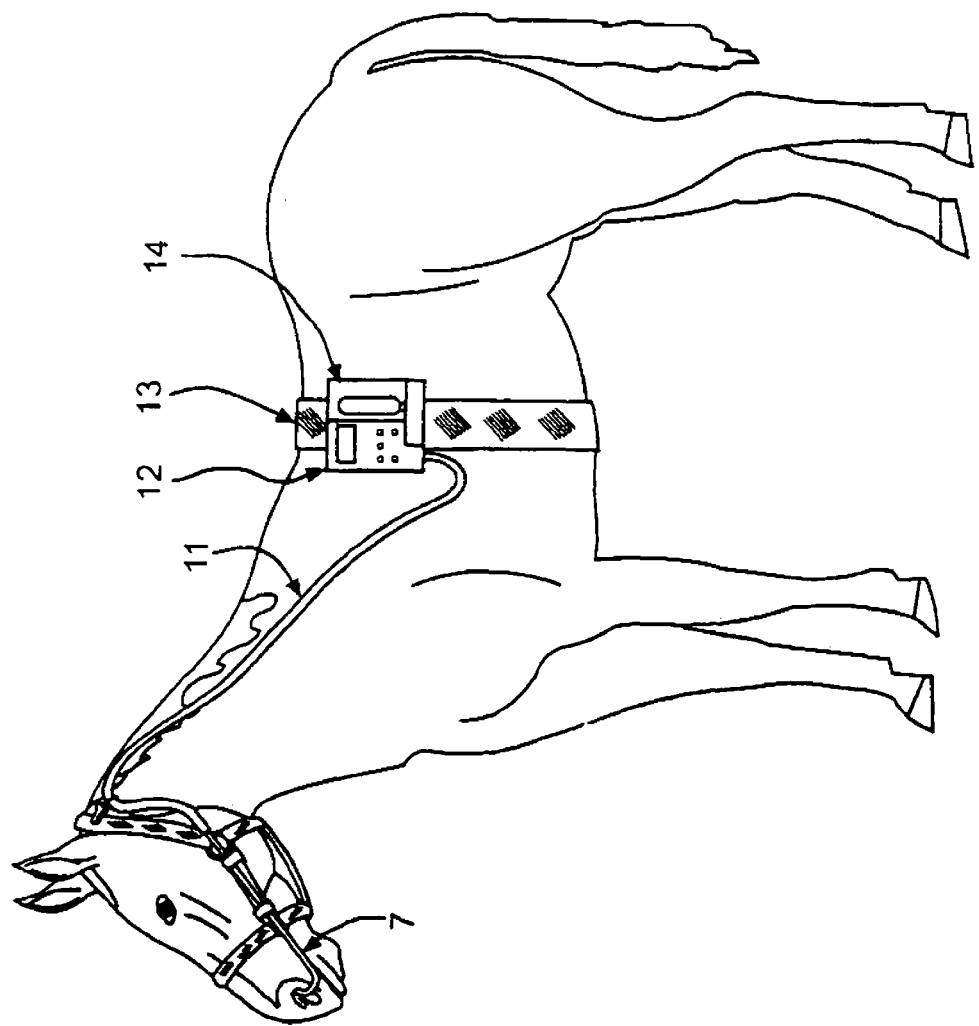
FIG. 4. illustrates a typical application in its complete form attached to a horse.

FIG. 4 shows a typical application in its complete form. The delivery device 12 is shown in a cradle 14 which attaches to a surcingle 13. This provides a convenient method of attaching the device to a horse.

Other delivery systems which may administer inhaled nitric oxide containing gas may include the delivery systems described in U.S. Pat. No. 5,765,548, which is herein incorporated by reference in its entirety. As such, several delivery devices may nasally administer the inhaled nitric oxide containing gas. The devices may administer a therapeutic level of nitric oxide gas, such as an inhale nitric oxide containing gas having a concentration of about 160 ppm to about 220 ppm nitric oxide. One apparatus for treating mucus accumulation in a mammal's airway may include a transportable container comprising a nitric oxide containing gas, such as the transportable delivery device 12, attached to the subject in FIG. 4. The apparatus may also include a nozzle in fluid flow communication with the container, wherein the nozzle is operable to deliver the nitric oxide containing gas to one or both nostrils of a mammal. An example of the nozzle is the J-shaped nozzle 7 shown in FIG. 4 in fluid communication with the delivery device 12.

The apparatus may also include means including a flow meter for determining a physiological acceptable quantity of the nitric oxide containing gas to be delivered into the mammal's airway from the nozzle. Such a flow meter may be used to deliver nitric oxide containing gas having a concentration of about 160 ppm to about 220 ppm nitric oxide. The physiological acceptable quantity of the nitric oxide containing gas may correspond to the mammal's respiratory tidal volume, as described in the delivery mechanics described in FIGS. 1-4.

The apparatus may also include an endoscope for determining the presence of mucus accumulation in the airway. This endoscope may communicate with the flow meter in order to deliver the nitric oxide containing gas when it detects a sufficient level of mucus accumulation.

In yet another embodiment of the invention, a kit or system may be provided for the treatment of mucus accumulation would comprise the a pressurized cylinder or canister containing gNO source and a label affixed to the cylinder or canister indicating that use of gNO as a mucolytic agent for the treatment of excess mucus accumulation.

Thus, a system may be assembled including a container comprising a nitric oxide containing gas and a visible label affixed to the container. The label may indicate that the nitric oxide containing gas is suitable for reducing mucus accumulation in a mammal's airway. Thus, a nitric oxide containing gas may be packaged and sold for the therapeutic use of reducing mucus accumulation in a mammal's airway. The label may also provide instructions for delivery of the nitric oxide containing gas and/or instructions for therapeutic treatments of mucus accumulation. As explained with reference to the human and equine models, the nitric oxide containing gas may have a concentration of about 160 ppm to about 10,000 ppm nitric oxide.

The example and figures describe the manner and process of nasal administration of gNO to an equine to reduce excess mucus accumulation according to the present invention. While embodiments of the present invention have been shown and described, various modifications may be made without departing from the scope of the invention. The invention, therefore, should not be limited, except to the following claims, and their equivalents.

The invention claimed is:

1. A method of treating excess mucus accumulation in a mammal's airway comprising:
   providing a pressurized source of nitric oxide containing gas; and
   administering through inhalation a therapeutically effective amount of nitric oxide containing gas to a mammal exhibiting excess mucus accumulation in the mammal's airway, wherein the nitric oxide containing gas is administered substantially coincident with the inspiration of the mammal, resulting in the flow of non-viscous liquids and mucus reduction.

2. The method of claim 1, further comprising the step of regulating a flow rate of the nitric oxide containing gas depending on the mammal's respiratory tidal volume.

3. The method of claim 2, wherein the concentration of nitric oxide gas in the mammal's airway ranges from about 160 ppm to about 220 ppm.

4. The method of claim 1, wherein the administration of the nitric oxide containing gas is timed according to a synchronous parameter of the mammal's respiratory cycle.

5. The method of claim 4, wherein the synchronous parameter is selected from a group consisting of rate of flow of gas directed toward the mammal's airway, pressure change at the initiation of a breath, the synchronous movement of the laryngeal, and the synchronous motion of the chest wall.

6. The method of claim 1, wherein the therapeutically effective amount of nitric oxide containing gas is sufficient to reduce an amount of mucus in the mammal's airways by at least 50%.

7. The method of claim 1, wherein the therapeutically effective amount of nitric oxide containing gas is sufficient to effect mucolysis within thirty minutes.

8. The method of claim 1, wherein the mammal is a horse.

9. A method of treating excess mucus accumulation in a mammal's airway comprising:
   identifying a mammal exhibiting excess mucus accumulation;
   determining the severity of mucus accumulation in the mammal;
   providing a source of nitric oxide containing gas; and
   administering through inhalation the nitric oxide containing gas using a distinct therapeutic profile corresponding to the severity of mucus accumulation in the mammal, resulting in the flow of non-viscous liquids and mucus reduction.

10. The method of claim 9, wherein the severity of mucus accumulation is scored from 0 to 5, with 5 indicating a most severe condition.

11. The method of claim 9, wherein the distinct therapeutic profile is selected from a pre-determined set of therapeutic profiles.

12. The method of claim 11, wherein the distinct therapeutic profile comprises therapeutic parameters selected from a group consisting of flow rate of nitric oxide containing gas, duration of administration of nitric oxide containing gas, number of breaths for which nitric oxide containing gas is to be administered, and concentrations of therapeutic NO delivered to the airways.

13. The method of claim 9, wherein the mammal is a horse.

14. A method of treating excess mucus accumulation in a mammal's airway comprising:
   administering through inhalation a therapeutically effective amount of NO-releasing compounds to a mammal exhibiting excess mucus accumulation in the mammal's airway, resulting in the flow of non-viscous liquids and mucus reduction.

15. The method of claim 14, wherein the NO-releasing compounds is selected from a group consisting of S-nitrosothiols, S-nitroso-N-acetylpenicillamine, S-nitroso-L-cysteine, NONOates, nitroprusside, NO-ferredoxin, NO-heme complex, and nitrosoguanidine.

16. The method of claim 14, wherein the mammal is a horse.

17. The method of claim 14, wherein the therapeutically effective amount of NO-releasing compounds is sufficient to reduce an amount of mucus in the mammal's airways by at least 50%.

18. The method of claim 14, wherein the therapeutically effective amount of NO-releasing compounds sufficient to effect mucolysis within thirty minutes.

19. A method of treating excess mucus accumulation in a mammal's airway comprising:
   identifying a mammal exhibiting excess mucus accumulation;
   determining the severity of mucus accumulation in the mammal; and
   administering through inhalation NO-releasing compounds using a distinct therapeutic profile corresponding to the severity of mucus accumulation in the mammal, resulting in the flow of non-viscous liquids and mucus reduction.

20. The method of claim 19, wherein the NO-releasing compounds is selected from a group consisting of S-nitrosothiols, S-nitroso-N-acetylpenicillamine, S-nitroso-L-cysteine, NONOates, nitroprusside, NO-ferredoxin, NO-heme complex, and nitrosoguanidine.

21. The method of claim 19, wherein the severity of mucus accumulation is scored from 0 to 5, with 5 indicating a most severe condition.

22. The method of claim 19, wherein the distinct therapeutic profile is selected from a pre-determined set of therapeutic profiles.

23. The method of claim 19, wherein the mammal is a horse.

24. The method of claim 19, wherein the therapeutically effective amount of NO-releasing compounds is sufficient to reduce an amount of mucus in the mammal's airways by at least 50%.

25. The method of claim 19, wherein the therapeutically effective amount of NO-releasing compounds sufficient to effect mucolysis within thirty minutes.

* * * * *